United States Patent [19]

Mjalli et al.

[11] Patent Number: 5,756,527

[45] Date of Patent: *May 26, 1998

[54] IMIDAZOLE DERIVATIVES USEFUL AS MODULATORS OF MULTI DRUG RESISTANCES

[75] Inventors: Adnan M. M. Mjalli, Escondido; Sepehr Sarshar, Cardiff, both of Calif.

[73] Assignee: Ontogen Corporation, Carlsbad, Calif.

[*] Notice: The term of this patent shall not extend beyond the expiration date of Pat. No. 5,700,826.

[21] Appl. No.: 845,322

[22] Filed: Apr. 25, 1997

Related U.S. Application Data

[63] Continuation-in-part of Ser. No. 481,118, Jun. 7, 1995, Pat. No. 5,700,826.

[51] Int. Cl.$^6$ ............ A61K 31/415; C07D 233/02; C07D 233/04; C07D 233/61; C07D 233/56
[52] U.S. Cl. ............ 514/397; 514/398; 514/399; 514/402; 548/315.1; 548/326.1; 548/335.1; 548/343.1; 548/343.5
[58] Field of Search ............ 514/397, 402, 514/398, 399; 545/326.1, 315.1, 335.1, 343.1, 343.5

[56] References Cited

FOREIGN PATENT DOCUMENTS 0 564 409 A1  10/1993  European Pat. Off. .

OTHER PUBLICATIONS

Bradley et al., *Cancer Res.* 49: 2790–2796, 1989.
Raderer and Scheithaurer, *Cancer* 72: 3553–3563, 1993.
Juranka et al., *FASEB J.* 3: 2583–2592, 1989.
Krishnamachary and Center, *Cancer Res.* 53: 3658–3661, 1993.
Jones et al., *Cancer* (Suppl) 72: 3484–3488, 1993.
Krieg et al *Z Naturforsch teil* 22b, 132 1967.
Bader et al *J. Org. Chem* 31, 2319 1966.
Garro–Helion, F. et al *J. Org. Chem.* 58, 6109–6113, 1993.
Patel et al *J. Org. Chem.*, 42, 3903, 1977.
4,5-bis-(4-bromo-phenyl)-2-m-totyl-1H-imidazole, Beilstein Crossfire Database, CAS Registry No. 40783-95-7 (Page).

*Primary Examiner*—Floyd D. Higel
*Attorney, Agent, or Firm*—Frank S. Chow

[57] ABSTRACT

The present invention relates to imidazole derivatives having formula 1

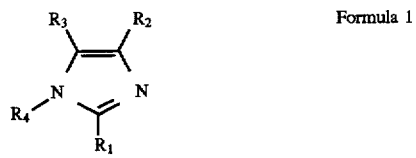

Formula 1 wherein:

$R_1$ is selected from the group consisting of: mono-, di-, and tri-substituted phenyl or thienyl, the substituents are selected from the group consisting of:
(i) substituted $C_{1-6}$ alkyl, substituted $C_{2-6}$ alkyloxy, wherein the substituents are selected from the group consisting of hydrogen or $C_{1-6}$ alkoxy;
(ii) $C_{1-11}CO_2R_5$, trans-CH=CHCO$_2R_5$, wherein $R_5$ is $C_{1-11}$ alkyl, or phenyl $C_{1-11}$ alkyl;

$R_2$ and $R_3$ are mono-, di, and tri-substituted phenyl wherein the substituents are independently selected from:
(i) halo;
(ii) $C_{1-6}$ alkyl-amino, or di($C_{1-6}$ alkyl)amino, and $R_4$ is hydrogen.

These compounds are useful for restoring the sensitivity of multidrug resistant cells to cancer chemotherapeutic agents.

40 Claims, No Drawings

IMIDAZOLE DERIVATIVES USEFUL AS MODULATORS OF MULTI DRUG RESISTANCES

This application is a continuation-in-part of application Ser. No. 08/481,118 filed Jun. 7th, 1995 now U.S. Pat. No. 5,700,826 issued Dec. 23, 1997.

FIELD OF INVENTION

The present invention provides novel imidazole derivatives, novel pharmaceutical compositions containing same, methods of their use, and methods of their manufacture. Such compounds are pharmacologically useful for restoring the sensitivity of multidrug resistant cells to cancer chemotherapeutic agents.

BACKGROUND OF INVENTION

A major problem in the treatment of malignancies of the blood and solid tumors is the emergence of tumor cell resistance to chemotherapeutic agents and the subsequent patient relapse (Bradley et al., Cancer Res. 49: 2790–2796, 1989; Raderer and Scheithaurer, Cancer 72: 3553–3563, 1993). This resistance causes cancer victims to fail to respond to any antitumor agent, since the transformed tumor cells tend to exhibit clinical resistance to many drugs. The emergence of the resistant cells to multiple chemotherapeutic agents occurs either at the initial presentation (intrinsic resistance) or at the time of relapse (acquired resistance). Both of these phenomena are known as multi-drug resistance (MDR). MDR is associated with certain alterations in tumor cells resulting in reduced intracellular anticancer drug accumulation, including reduced membrane permeability and increased removal of drug from the cell via an energy-dependent efflux mechanism. Studies of this mechanism have led to the characterization of genes capable of conferring resistance to chemotherapeutic agents. One of these genes, the P-glycoprotein or MDR1 gene, has been strongly implicated since overexpression of this gene can lead to resistance to anthracyclines, vinca alkaloids, and podophyllins, all important chemotherapeutic agents. MDR1 encodes a 170 kDa membrane glycoprotein (gp-170 or Pgp) that acts as an ATP-dependent efflux pump, transporting a number of unrelated organic compounds out of the cell (Juranka et al., FASEB J 3: 2583–2592, 1989). The level of expression of gp-170 has been shown to correlate with the degree of drug resistance (Raderer and Scheithaurer, Cancer 72: 3553–3563, 1993). gp-170 appears to act as a pump that actively extrudes a wide variety of structurally unrelated compounds, including a full range of antineoplastic drugs. Another ATP-dependent membrane efflux pump, the product of the MRP gene, has also been implicated in the MDR phenomenon (Krishnamachary and Center, Cancer Res. 53: 3658–3661, 1993), as have other ATP-dependent and enzymatic mechanisms.

Drugs of proven antitumor chemotherapeutic value to which MDR has been observed include vinblastine, vincristine, etoposide, teniposide, doxorubicin (adriamycin), daunorubicin, pliamycin (mithramycin), and actinomycin D (Jones et al., Cancer (Suppl) 72: 3484–3488, 1993). Many tumors are intrinsically multi-drug resistant (e.g., adenocarcinomas of the colon and kidney) while other tumors acquire MDR during the course of therapy (e.g., neuroblastomas and childhood leukemias).

A variety of structurally diverse agents have been identified which can restore partially or sometimes completely the normal drug sensitivity to some MDR tumor cells. It is assumed that these chemosensitizers are effective as a result of their ability to interfere with gp-170, causing a reversal in the increase in drug efflux. Among these agents are calcium channel blockers (e.g., verapamil and nifedipine), calmodulin inhibitors (e.g., trifluoperazine), antibiotics (e.g., erythromycin), cardiovascular agents (e.g., quinidine), non-cytotoxic analogs of anthracyclines and vinca alkaloids, the clinically useful immunosuppressants cyclosporin A (and analogs thereof) and FK-506 (and analogs thereof), and derivatives of cyclopeptides (Lum et al., Cancer (Suppl) 72: 3502–3514, 1993). However, at the present time, none of these agents has provided a significant contribution to the chemotherapeutic index for the treatment of cancer due to their significant pharmacological effects on other organ systems. An effective therapeutic agent for the reversal of MDR needs to have efficacy against the membrane pump as well as lack significant toxicity and other non-specific pharmacological effects.

The present invention describes a family of novel substituted imidazole derivatives that are effective in increasing the sensitivity of tumor cells resistant to anticancer chemotherapeutic agents, such as doxorubicin (DOX), taxol, and vinblastine (VLB), and enhancing the sensitivity of multi-drug resistant cells. These compounds have the effect of reducing the resistance of MDR tumor cells, and potentiating the sensitivity of cells to antitumor drugs, such as DOX, taxol, and VLB. These compounds are expected to have broad application in the chemotherapy of cancer.

It is an object of this invention, therefore, to provide compounds that have sufficient activity to sensitize multi-drug resistant tumor cells to antineoplastic agents.

It is an additional object of this invention to provide a method of sensitizing multi-drug resistant tumor cells using the novel compounds of the present invention.

A further object is to provide a method of treatment of MDR or drug-sensitive tumor cells by administering a sufficient amount of a compound of the present invention, prior to, together with, or subsequent to the administration of an antitumor chemotherapeutic agent.

A further object is to provide pharmaceutical compositions for increasing the sensitivity of tumor cells to antitumor chemotherapeutic agents and thus for the treatment of tumors that are susceptible to anti-cancer chemotherapeutic agents but have become resistant to such chemotherapy.

These and other objects will be apparent from the following description.

SUMMARY OF THE INVENTION

The novel compounds of this invention have the general formula:

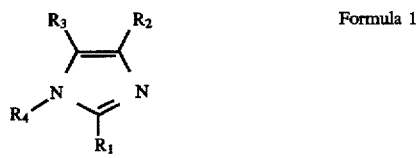

Formula 1 in which $R_1$, $R_2$, $R_3$, and $R_4$ are defined hereinafter. These compounds including the corresponding pharmaceutically acceptable salts or prodrug thereof are capable of restoring sensitivity to multi-drug resistant tumor cells. It is an object of this invention to provide compounds that have sufficient activity to sensitize multi-drug resistant tumor cells to antineoplastic agents.

It is an additional object of this invention to provide a method of sensitizing multi-drug resistant tumor cells using the novel compounds of the present invention.

A further object is to provide a method of treatment of MDR or drug-sensitive tumor cells by administering a sufficient amount of a compound of the present invention, prior to, together with, or subsequent to the administration of an antitumor chemotherapeutic agent.

A further object is to provide pharmaceutical compositions for increasing the sensitivity of tumor cells to antitumor chemotherapeutic agents and thus for the treatment of tumors that are susceptible to anti-cancer chemotherapeutic agents but have become resistant to such chemotherapy.

DETAILED DESCRIPTION OF THE INVENTION

The present invention encompasses compounds of general structural Formula 1

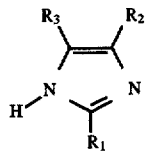

Formula 1 or a pharmaceutically acceptable salt, or prodrug thereof wherein:

R is selected from the group consisting of: mono-,di-,and tri-substituted phenyl or thienyl, the substituents are selected from the group consisting of:

(i) substituted $C_{1-6}$ alkyl, substituted $C_{2-6}$ alkyloxy, wherein the substituents are selected from the group consisting of H or $C_{1-6}$ alkoxy, (ii) $C_{1-11}CO_2R_5$, trans-CH=CHCO$_2R_5$, wherein $R_5$ is $C_{1-11}$ alkyl, or phenyl $C_{1-11}$ alkyl.

$R_2$ and $R_3$ are mono-, di, and tri-substituted phenyl wherein the substituents are independently selected from:

(i) halo;

(ii) $C_{1-6}$ alkyl-amino, or di($C_{1-6}$ alkyl)amino, and $R_4$ is hydrogen.

Novel compounds of the present invention include but are not limited to the following compounds:

A compound according to formula 1 wherein $R_1$ is 4-[(trans-2-isopropyloxycarbonyl)-ethenyl]-phenyl; $R_2$ and $R_3$ are 4-(dimethylamino)-phenyl; and $R_4$ is hydrogen.

A compound according to Formula 1 wherein $R_1$ is 4-[(trans-2-tert-butyloxycarbonyl)-ethenyl]-phenyl; $R_2$ and $R_3$ are 4-(dimethylamino)-phenyl; and $R_4$ is hydrogen.

A compound according to Formula 1 wherein $R_1$ is 4-[(trans-2-methoxycarbonyl)-ethenyl]-phenyl; $R_2$ is 4-(methylamino)-phenyl and $R_3$ are 4-(diethylamino)-phenyl; and $R_4$ is hydrogen.

A compound according to Formula 1 wherein $R_1$ is 4-[(trans-2-isopropyloxycarbonyl)-ethenyl]-phenyl; $R_2$ is 4-(methylamino)-phenyl and $R_3$ are 4-(diethylamino)-phenyl; and $R_4$ is hydrogen.

A compound according to Formula 1 wherein $R_1$ is 4-[(trans-2-methoxycarbonyl)-ethenyl]-phenyl; $R_2$ is 4-(methylamino)-phenyl and $R_3$ are 4-(dimethylamino)-phenyl; and $R_4$ is hydrogen.

A compound according to Formula 1 wherein $R_1$ is 4-[(trans-2-methoxycarbonyl)-ethenyl]-phenyl; $R_2$ is 4-(methylamino)-phenyl and $R_3$ are 4-(n-propylmethylamino)-phenyl; and $R_4$ is hydrogen.

A compound according to Formula 1 wherein $R_1$ is 4-[(trans-2-methoxycarbonyl)-ethenyl]-phenyl; $R_2$ is 4-(methylamino)-phenyl and $R_3$ are 4-di(n-propylamino)-phenyl; and $R_4$ is hydrogen.

A compound according to Formula 1 wherein $R_1$ is 4-[(trans-2-methoxycarbonyl)-ethenyl]-phenyl; $R_2$ is 4-(methylamino) -phenyl and $R_3$ are 4-di(n-butylamino)-phenyl; and $R_4$ is hydrogen.

A compound according to Formula 1 wherein $R_1$ is 4-[(trans-2-methoxycarbonyl)-ethenyl]-phenyl; $R_2$ and $R_3$ are 4-(methylamino)-phenyl; and $R_4$ is hydrogen.

A compound according to Formula 1 wherein $R_1$ is 4-[(trans-2-methoxycarbonyl)-ethenyl]-phenyl; $R_2$ is 4-(isopropylamino)-phenyl and $R_3$ are 4-(methylamino)-phenyl; and $R_4$ is hydrogen.

A compound according to Formula 1 wherein $R_1$ is 4-[(trans-2-methoxycarbonyl)-ethenyl]-phenyl; $R_2$ is 4-(tert-butylamino)-phenyl and $R_3$ are 4-(methylamino)-phenyl; and $R_4$ is hydrogen.

A compound according to Formula 1 wherein $R_1$ is 4-[(trans-2-methoxycarbonyl)-ethenyl]-phenyl; $R_2$ and $R_3$ are 4-di(ethylamino)-phenyl; and $R_4$ is hydrogen.

A compound according to Formula 1 wherein $R_1$ is 4-[(trans-2-methoxycarbonyl)-ethenyl]-phenyl; $R_2$ is 4-di(ethylamino)-phenyl and $R_3$ are 4-di(methylamino)-phenyl; and $R_4$ is hydrogen.

A compound according to Formula 1 wherein $R_1$ is 4-[(trans-2-methoxycarbonyl)-ethenyl]-phenyl; $R_2$ is 4-(amino)-phenyl and $R_3$ are 4-di(methylamino)-phenyl; and $R_4$ is hydrogen.

A compound according to Formula 1 wherein $R_1$ is 4-[(trans-2-methoxycarbonyl)-ethenyl]-phenyl; $R_2$ is 4-(amino)-phenyl and $R_3$ are 4-di(ethylamino)-phenyl; and $R_4$ is hydrogen.

A compound according to Formula 1 wherein $R_1$ is 4-[(trans-2-methoxycarbonyl)-ethenyl]-phenyl; $R_2$ is 4-(fluoro)-phenyl and $R_3$ are 4-(methylamino)-phenyl; and $R_4$ is hydrogen.

A compound according to Formula 1 wherein $R_1$ is 3-[(trans-2-methoxycarbonyl)-ethenyl]-phenyl; $R_2$ and $R_3$ are 4-di(methylamino)-phenyl; and $R_4$ is hydrogen.

A compound according to Formula 1 wherein $R_1$ is 3-[(trans-2-methoxycarbonyl)-ethenyl]-4-methoxy-phenyl; $R_2$ and $R_3$ are 4-di(methylamino)-phenyl; and $R_4$ is hydrogen.

A compound according to Formula 1 wherein $R_1$ is 5-[(trans-2-methoxycarbonyl)-ethenyl]-2-methoxy-phenyl; $R_2$ and $R_3$ are 4-di(methylamino)-phenyl; and $R_4$ is hydrogen.

A compound according to Formula 1 wherein $R_1$ is 5-[(trans-2-methoxycarbonyl)-ethenyl]-3,4-dimethoxy-phenyl; $R_2$ and $R_3$ are 4-di(methylamino)-phenyl; and $R_4$ is hydrogen.

A compound according to Formula 1 wherein $R_1$ is 3-[(trans-2-methoxycarbonyl)-ethenyl]-4-fluoro-phenyl; $R_2$ and $R_3$ are 4-di(methylamino)-phenyl; and $R_4$ is hydrogen.

A compound according to Formula 1 wherein $R_1$ is 3-[(trans-2-methoxycarbonyl)-ethenyl]-4-fluoro-phenyl; $R_2$ is 4-(methylamino)-phenyl; and $R_3$ is 4-di(methylamino)-phenyl; and $R_4$ is hydrogen.

A compound according to Formula 1 wherein $R_1$ is 4-[(trans-2-methoxycarbonyl)-ethenyl]-2-fluoro-phenyl; $R_2$ and $R_3$ are 4-di(methylamino)-phenyl; and $R_4$ is hydrogen.

A compound according to Formula 1 wherein $R_1$ is 4-[(trans-2-methoxycarbonyl)-ethenyl]-thienyl; $R_2$ and $R_3$ are 4-di(methylamino)-phenyl; and $R_4$ is hydrogen.

A compound according to Formula 1 wherein $R_1$ is 3-[(trans-2-methoxycarbonyl)-ethenyl]-thienyl; $R_2$ and $R_3$ are 4-di(methylamino)-phenyl; and $R_4$ is hydrogen.

A compound according to Formula 1 wherein $R_1$ is 4-(n-propylmethylether)-phenyl; $R_2$ and $R_3$ are 4-di(methylamino)-phenyl; and $R_4$ is hydrogen.

A compound according to Formula 1 wherein $R_1$ is 4-[(trans-2-isopropyloxycarbonyl)-ethenyl]-2-methoxyphenyl; $R_2$ and $R_3$ are 4-di(methylamino)-phenyl; and $R_4$ is hydrogen.

A compound according to Formula 1 wherein $R_1$ is 4-[(trans-2-isopropyloxycarbonyl)-ethenyl]-thienyl; $R_2$ and $R_3$ are 4-di(methylamino)-phenyl; and $R_4$ is hydrogen.

A compound according to Formula 1 wherein $R_1$ is 4-[(trans-2-benzyloxycarbonyl)-ethenyl]-phenyl; $R_2$ and $R_3$ are 4-di(methylamino)-phenyl; and $R_4$ is hydrogen.

A compound according to Formula 1 wherein $R_1$ is 4-[(trans-2-phenylethyloxycarbonyl)-ethenyl]-phenyl; $R_2$ and $R_3$ are 4-di(methylamino)-phenyl; and $R_4$ is hydrogen.

A compound according to Formula 1 wherein $R_1$ is 4-(3-ethoxypropyl)-phenyl; $R_2$ and $R_3$ are 4-di(methylamino)-phenyl; and $R_4$ is hydrogen.

A compound according to Formula 1 wherein $R_1$ is 4-butyloxyphenyl; $R_2$ and $R_3$ are 4-di(methylamino)-phenyl; and $R_4$ is hydrogen.

A compound according to Formula 1 wherein $R_1$ is 4-(2-methoxyethoxy)phenyl; $R_2$ and $R_3$ are 4-di(methylamino)-phenyl; and $R_4$ is hydrogen.

A compound according to Formula 1 wherein $R_1$ is 3-methoxy-4-(2-methoxyethoxy)-phenyl; $R_2$ and $R_3$ are 4-di(methylamino)-phenyl; and $R_4$ is hydrogen.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonyl, decyl, iso-propyl (i-Pr), iso-butyl (i-Bu), tert-butyl (t-Bu), sec-butyl (s-Bu), iso-pentyl, and the like, as well as saturated alicyclic hydrocarbon groups having the specified number of carbon atoms, e.g., cyclopentyl, cyclohexyl, and the like. "Alkyloxy" (or "alkoxy") represents an alkyl group having the indicated number of carbon atoms attached through the oxygen bridge, e.g., methoxy, ethoxy, propyloxy, and the like. The carbon-carbon double bonds may have either the cis- or trans-configuration.

The term "halo" means fluoro, chloro, bromo, or iodo.

The term "prodrug" refers to a compound according to formula 1 that is made more active in vivo.

Pharmaceutically acceptable salts of the compounds of formula 1, where a basic or acidic group is present in the structure, are also included within the scope of this invention. Salts derived from pharmaceutically acceptable organic non-toxic bases include salts of primary, secondary, and tertiary amines, substituted amines including naturally occurring substituted amines, cyclic amines, and basic ion-exchange resins, such as arginine, betaine, caffeine, choline, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When a basic group is present, such as amino or a basic heteroaryl radical, such as pyridyl, an acidic salt, such as hydrochloride, hydrobromide, acetate, maleate, pamoate, methanesulfonate, p-toluenesulfonate, and the like, can be used as the dosage form.

Also, in the case of the —COOH being present, pharmaceutically acceptable esters can be employed, e.g., methyl, tert-butyl, pivaloyloxymethyl, and the like, and those esters known in the art for modifying solubility or hydrolysis characteristics for use as sustained release or prodrug formulations.

In addition some of the compounds of the instant invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other clinician.

The compounds of the present invention are conveniently prepared using either solid-phase or solution phase synthetic methods. These two methods are described generally below and depicted in the following reaction Schemes. Where appropriate, the synthetic methods utilize readily available starting materials, reagents, and conventional synthetic procedures. In these reactions, it is also possible to make use of variants which are themselves known to those of ordinary skill in this art, but are not mentioned in greater detail.

Compounds of the present invention are synthesized according to Scheme 1.

A series of diones (2) were reacted with a series of aldehydes (3) in the presence of ammonium acetate in acetic acid at high temperature (according to modified literature procedure by Krieg et al *Z Naturforsch teil* 1967, 22b, 132) and produced the desired compounds of general Formula 1 as shown in Scheme 1

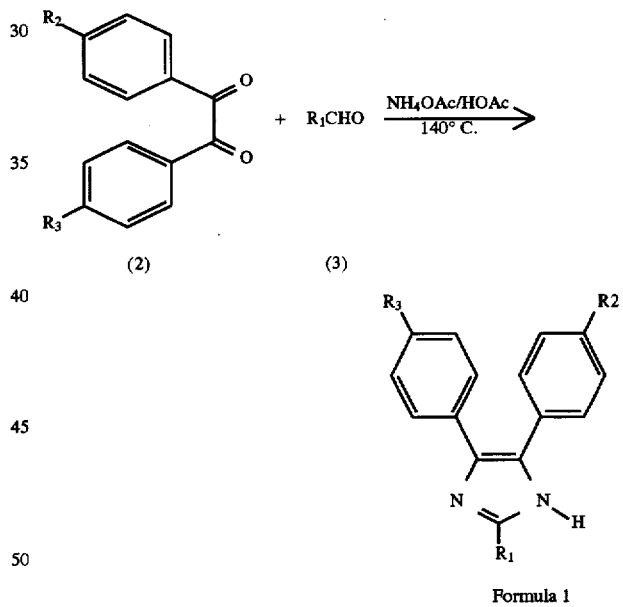

The diones (2) and the aldehydes (3) have been synthesized according to Method A and B respectively:

Method A. General Procedure for the Preparation of Diones:

There are two methods by which these diones were synthesized namely:

Method 1

4,4'-difluorodione 4 was reacted with a series of amines ($R_1R_2NH$) using an appropriate base such as $K_2CO_3$, $Na_2CO_3$, $Et_3N$, diisopropylethylamine (DIEA), etc., at elevated temperature (60°–150° C.) in an appropriate solvent such as alcohol, acetonitrile, N,N-dimethylaminoformamide (DMF), dimethylsulfoxide (DMSO) and provided the mono-amino-diones 5 (procedure Bader et al *J. Org. Chem.* 1966, 31, 2319). The mono-aminodiones 5 were further reacted with another amine (R₃R₄NH) under the same conditions to afford the desired diones 6 as shown in Scheme 2. This procedure allows for the synthesis of unsymmetrical diones 6 (wherein $R_1R_2NH$ is different from $R_3R_4NH$). This chemistry was carried out using 1–1.5 equivalent of $R_1R_2NH$ and upon the completion of the reaction another equivalent of different amine ($R_3R_4NH$) was added to the reaction mixture to provide the desired unsymmetrical diones (Scheme 2).

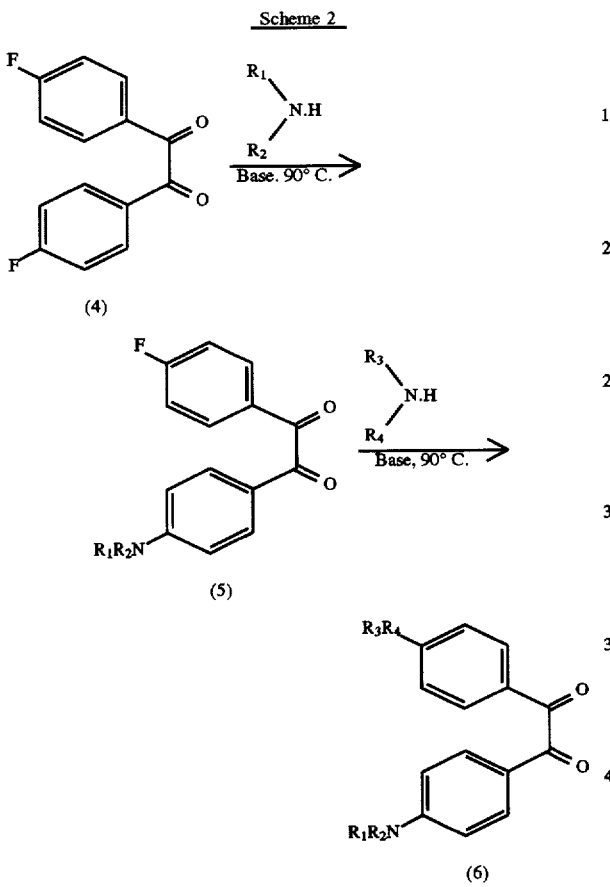

Unsymmetrcal diones were prepared according to the following procedure: To a solution of 4,4'-difluorobenzil in DMSO (0.5M) was added 1.2 equiv of amine $R_1R_2NH$ and 1:2 equiv of potassium carbonate. The resulting mixture was stirred in a 90° C. oil bath for 6–15 hours (TLC monitoring). After completion, the mixture was diluted with ether and extracted with 3M hydrochloric acid (x5) to remove the small amount of product resulted from the di-displacement. The organic layer was then washed with 6M hydrochloric acid until no more desired product in the ether layer (5 times). The aqueous layer was neutralized to pH 8 with 6M aqueous sodium hydroxide and it was extracted with dichloromethane. The organic layers were dried ($Na_2SO_4$), evaporated to obtain compound 4-amino,4'-fluorobenzil. This procedure was repeated with the second amine $R_3R_4NH$ (normally 2–3 equiv) and a simple workup by diluting the reaction mixture into ether and washed with water to remove DMSO. 4,4'-diaminobenzil was thus obtained (50–90% overall depending amines used) in high purity.

For symmetrical diones (wherein $R_1R_2NH$ is equal to $R_2R_3NH$) the following procedure was followed:

To a solution of 4,4'-difluorobenzil in DMSO (0.5M) was added 2-3 equiv of amine $R_1R_2NH$ and 2-3 equiv of potassium carbonate. The resulting mixture was stirred in a 90° C. oil bath for 6–15 hours (TLC monitoring). After completion, the mixture was diluted into ether and washed with water to remove DMSO. The desired diones 6 were obtained (50–90% overall depending amines used) in high purity. The following compounds have been synthesized by method 1.

7) 4-N,N-diethylamino-4'-N-methylaminobenzil

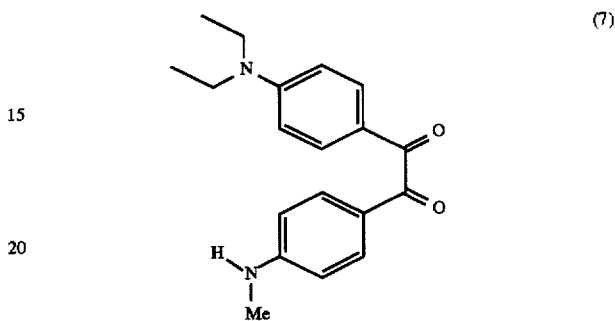

Compound 7 was prepared in 42% yield. ¹HMR (400 MHz, CDCl₃) δ1.15 (t, 6H), 2.85 (s, 3H), 3.37 (q, 4H), 4.40 (s, 1H), 6.50 (d, 2H), 6.57 (d, 2H), 7.78 (d, 4H).

8) 4-N,N-dimethylamino-4'-N-methylaminobenzil

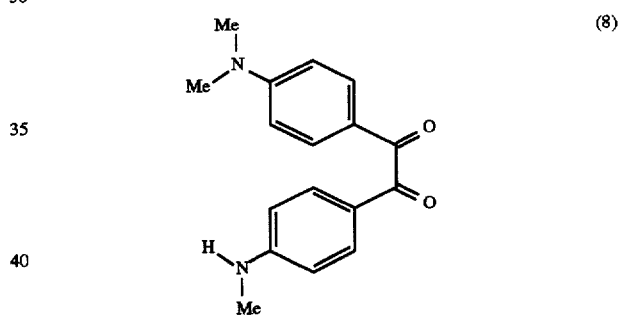

Compound 8 was prepared in 42% yield. ¹HMR (400 MHz, CDCl₃) δ2.80 (s, 3H), 3.03 (s, 6H), 4.48 (br s, 1H), 6.48 (d, 2H), 6.59 (d, 2H), 7.75 (d, 2H), 7.79 (d, 2H).

9) 4-N-methylamino-4'-N-methyl-N-propylamino-benzil

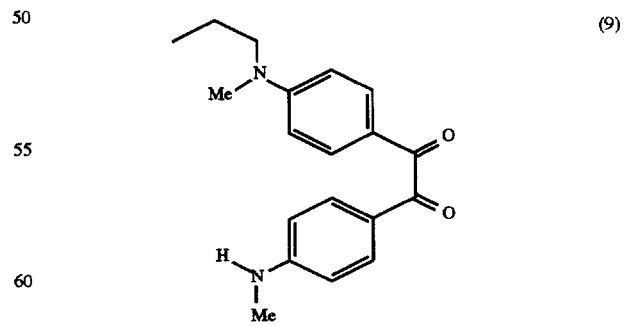

Compound 9 was prepared in 42% yield. ¹HMR (400 MHz, CDCl₃) δ0.87 (t, 3H), 1.57 (m, 2H), 2.80 (s, 3H), 2.97 (s, 3H), 3.30 (t, 2H), 4.60 (br s, 1H), 6.46 (d, 2H), 6.56 (d, 2H), 6.54 (d, 2H), 7.77 (d, 2H).

10) 4-N,N-dipropylamino-4'-N-methylaminobenzil

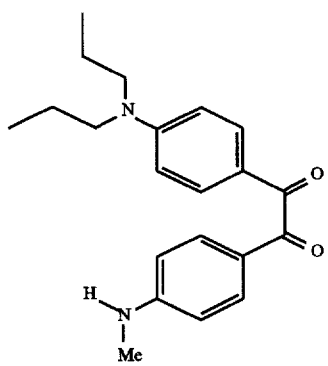
(10)

Compound 10 was prepared in 42% yield. ¹HMR (400 MHz, CDCl₃) δ0.89(t, 6H), 1.58 (m, 4H), 2.84 (d, 3H), 3.26 (t, 4H), 4.44 (br s, 1H), 6.49 (d, 2H), 6.54 (d, 2H), 7.75 (d, 2H), 7.77 (d, 2H).

11) 4-N,N-dbutylamino-4'-N-methylaminobenzil

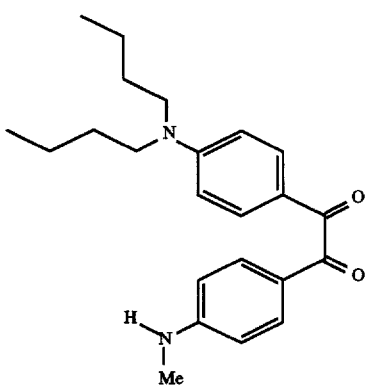
(11)

Compound 11 was prepared in 42% yield. ¹HMR (400 MHz, CDCl₃) δ0.91(t, 6H), 1.31 (m, 4H), 1.53 (m, 4H), 2.84 (d, 3H), 3.29 (t, 4H), 4.44 (br s, 1H), 6.49 (d, 2H), 6.54 (d, 2H), 7.75 (d, 2H), 7.77 (d, 2H).

12) 4,4'-bis(methylamino)benzil

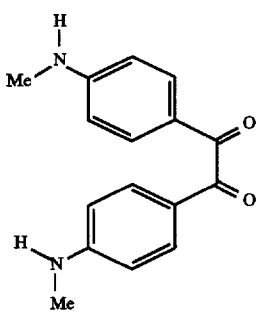
(12)

¹HMR (400 MHz, CDCl₃) δ2.80 (s, 6H), 4.64 (br s, 2H), 6.48 (d, 4H), 7.73 (d, 4H).

13) 4-N-methylamino-4'-N-isopropylaminobenzil

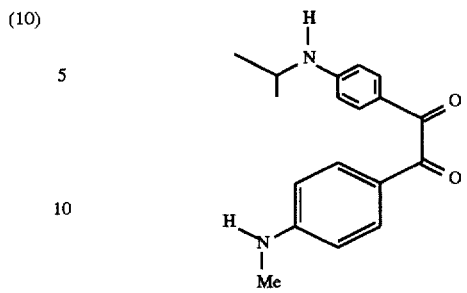
(13)

Compound 13 was prepared in 42% yield. ¹HMR (400 MHz, CDCl₃) δ1.18 (d, 6H), 2.83 (d, 3H), 3.65 (m, 1H), 4.28 (br d, 1H), 4.54 (br s, 1H), 6.47 (d, 2H), 6.49 (d, 2H), 7.74 (d, 2H), 7.76 (d, 2H).

14) 4-N-tert-butylamino-4'-N-methylaminobenzil

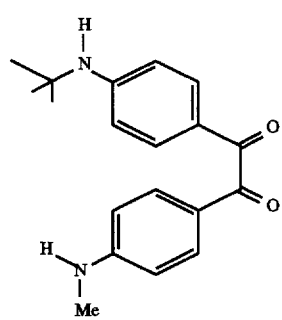
(14)

Compound 14 was prepared in 42% yield. HMR (400 MHz, CDCl₃) δ1.38 (s, 6H), 2.83 (d, 3H), 4.40 (br d, 1H), 4.52 (br s, 1H), 6.49 (d, 2H), 6.58 (d, 2H), 7.71 (d, 2H), 7.76 (d, 2H).

15) 4,4'bis(N,N-diethylamino)benzil

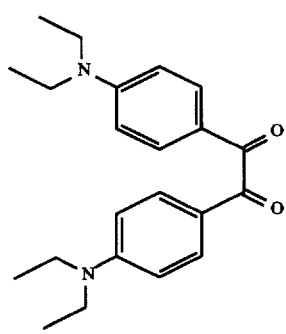
(15)

Compound 15 was prepared quantitatively. ¹HMR (400 MHz, CDCl₃) δ1.18 (t, 12H), 3.40 (q, 8H), 6.60 (d, 4H), 7.80 (d, 4H).

16) 4-N,N-diethylamino-4'-N,N-dimethylaminobenzil

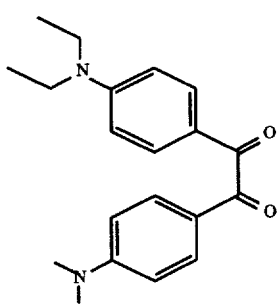
(16)

Compound 16 was prepared in 92% yield. ¹HMR (400 MHz, CDCl₃) δ1.15 (t, 6H), 3.02 (s, 6H), 3.38 (q, 4H), 6.57 (d, 2H), 6.60 (d, 2H), 7.78 (d, 2H), 7.81(d, 2H).

17) 4-fluoro-4'-N-methylbenzil

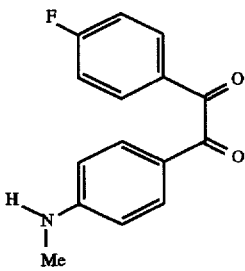
(17)

Compound 17 was prepared in 42% yield. ¹HMR (400 MHz, CDCl₃) δ2.88 (d, 3H), 4.50 (s, 1H), 6.54 (d, 2H), 7.11 (d, 2H), 7.13 (d, 2H), 7.77 (d, 2H), 7.96 (d, 1H), 7.99 (d, 1H).

18) 4-N,N-diallylamino-4'-fluorobenzil

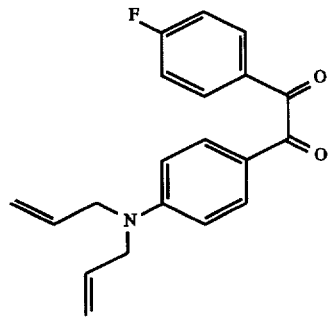
(18)

Compound 18 was prepared in 63% yield. ¹HMR (400 MHz, CDCl₃) δ3.95 (d, 4H), 5.12 (m, 4H), 5.78 (m, 2H), 6.63 (d, 2H), 7.09 (d, 1H), 7.10 (d, 1H), 7.75 (d, 2H), 7.96 (m, 2H).

Method 2

Reaction of 4-fluoro,4'-diallylamino dione (19) with a series of amines R₃R₄NH as described in Method 1 provided diones of Formula (20). These diones were reacted with Pd(PPh₃)₄ in the presence of N,N-dimethylbarbituric acid (NDMBA) in methylene chloride at room temp. to provide the desired diones of general Formula (21) as own in Scheme 3 (according to modified procedure by Garro-Helion, F. et al (*J. Org. Chem.* 1993, 58, 6109–6113).

Scheme 3

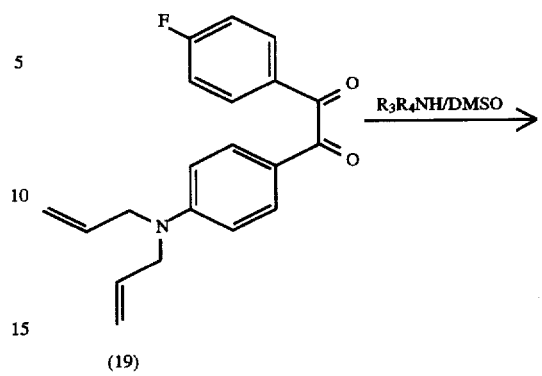
(19)

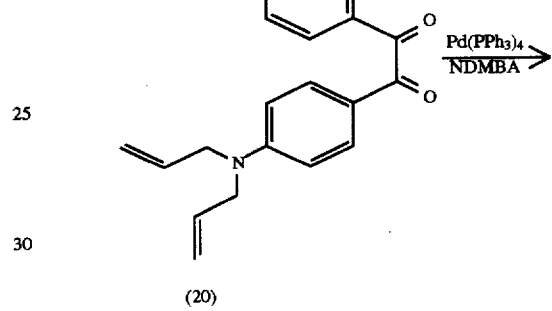
(20)

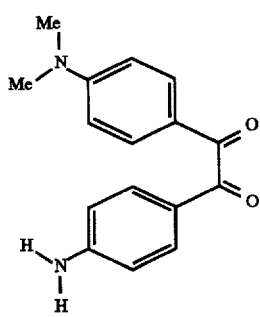
(21)

The following compounds have been synthesized using method 2:

22) 4-amino-4'-N,N-dimethylaminobenzil

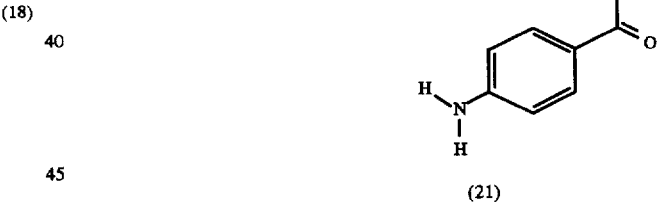
(22)

Compound 22 was prepared in 80% yield. ¹HMR (400 MHz, CDCl₃) δ3.00 (s, 6H), 4.30 (s, 2H), 6.57 (d, 2H), 6.59 (d, 2H), 7.74 (d, 2H), 7.79 (d, 2H).

23) 4-amino-4'-N,N-diethylaminobenzil

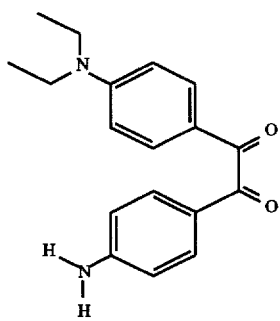

(23)

Compound 23 was prepared in 81% yield. ¹HMR (400 MHz, CDCl₃) δ1.15 (t, 6H), 3.37 (m, 4H), 4.30 (s, 2H), 6.57 (d, 4H), 7.74 (d, 2H), 7.76 (d, 2H).

Method B

General Method for the Synthesis of Aldehydes 27–38

Compounds of formula (24) wherein Ar is phenyl, thienyl were reacted with compound of formula (25) wherein EWG is an ester functionality to afford desired compounds of Formula (26) (Scheme 4) according to Patel et al (*J. Org. Chem.*, 1977, 42, 3903). These reactions may be carried out neat or in a solvent such as dimethylformamide (DMF), tetrahydrofuran (THF), toluene in the presence of a catalyst (e.g. Pd(OAc)₂, Pd(PPh₃)₄, Pd₂dba₃), a ligand (e.g. Ph₃P, Ph₃As, (o-tolyl)₃P) and a base (e.g. K₂CO₃, CsCO₃, Et₃N) at temperatures ranging from 23° C. to 130° C., for 1 to 60 hours.

Scheme 4

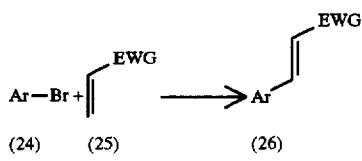

27) Butyl 4-formyl trans-cinnamate

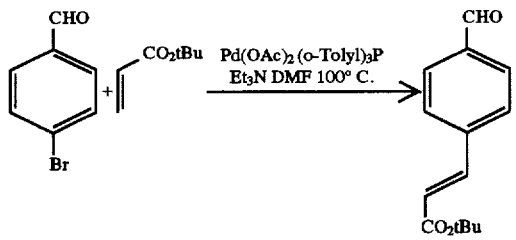

Compound 27 was prepared in 80% yield. ¹H NMR (400 MHz, CDCl₃) δ1.5 (s, 9H), 6.4 (d, 1H), 7.55 (d, 1H), 7.6 (d, 2H), (d, 2H), 9.95 (s, 1H).

28) Propyl 4-formyl trans-cinnamate

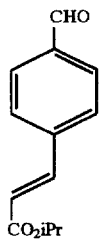

(28)

Compound 28 was prepared in 90% yield. ¹HMR (400 MHz, CDCl₃) δ1.30 (d, 6H), 5.10 (m, 1H), 6.50 (d, 1H), 7.63 (m, 3H), 7.85 (d, 2H), 9.98 (s, 1H).

29) Methyl 4-formyl trans-cinnamate

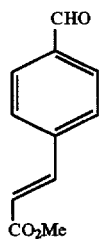

(29)

Compound 29 was prepared in 95% yield. HMR (400 MHz, CDCl₃) δ3.78 (s, 3H), 6.50 (d, 1H), 7.63 (m, 3H), 7.85 (d, 2H), 9.98 (s, 1H).

30) Methyl 3-formyl trans-cinnamate

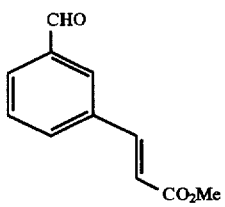

(30)

Compound 30 was prepared in 77% yield. ¹HMR (400 MHz, CDCl₃) δ3.80 (s, 3H), 6.50 (d, 1H), 7.54 (m, 1H), 7.70 (m, 2H), 7.84 (d, 1H), 8.00 (s, 1H), 10.00 (s, 1H).

31) Methyl 5-formyl-2-methoxy trans-cinnamate

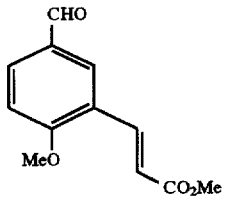

(31)

Compound 31 was prepared in 60% yield. ¹HMR (400 MHz, CDCl₃) δ3.79 (s, 3H), 3.98 (s, 3H), 6.56 (d, 1H), 7.00 (d, 1H), 7.85 (d, 1H), 7.94 (d, 1H), 8.00 (s, 1H), 9.87 (s, 1H).

32) Methyl 3-formyl-4-methoxy trans-cinnamate

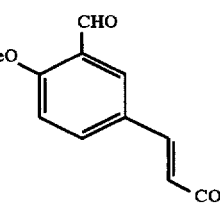

(32)

Compound 32 was prepared quantitatively. ¹HMR (400 MHz, CDCl₃) δ3.79 (s, 3H), 3.98 (s, 3H), 6.35 (d, 1H), 6.98 (d, 1H), 7.60 (d, 1H), 7.66 (dd, 1H), 7.96 (d, 1H), 10.21 (s, 1H).

33) Methyl 2,3-dimethoxy-5-formyl trans-cinnamate

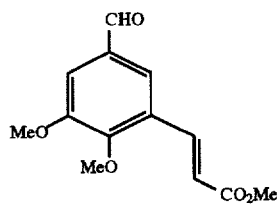

Compound 33 was prepared in 43% yield. ¹HMR (400 MHz, CDCl₃) δ3.80 (s, 3H), 3.90 (s, 3H), 3.95 (s, 3H), 6.52 (d, 1H), 7.41 (s, 1H), 7.61 (s, 1H), 7.95 (d, 1H), 9.87 (s, 1H).

34) Methyl 2-fluoro-5-formyl trans-cinnamate

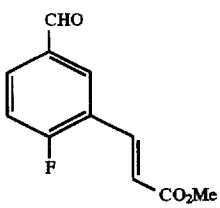

Compound 34 was prepared in 11% yield. ¹HMR (400 MHz, CDCl₃) δ3.80 (s, 3H), 6.60 (d, 1H), 7.24 (m, 1H), 7.79 (d, 1H), 7.87 (m, 1H), 8.04 (d, 1H), 9.98 (s, 1H).

35) Methyl 3-fluoro-4-formyl trans-cinnamate

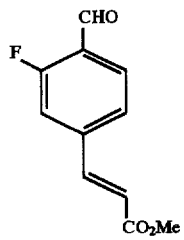

ompound 35 was prepared in 72% yield. ¹HMR (400 MHz, CDCl₃) δ3.80 (s, 3H), 6.49 (d, 1H), 7.27 (d, 1H), 7.37 (d, 1H), 7.61 (d, 1H), 7.85 (dd, 1H), 10.31 (s, 1H).

36) Methyl 3-[5-(2-formyl)thienyl] trans-propenoate

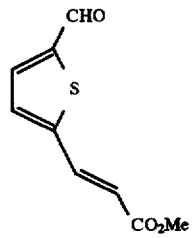

Compound 36 was prepared in 30% yield. ¹HMR (400 MHz, CDCl₃) δ3.80 (s, 3H), 6.37 (d, 1H), 7.28 (d, 1H), 7.65 (d, 1H), 7.71 (d, 1H), 9.87 (s, 1H).

37) Methyl 3-[4-(2-formyl)thienyl] trans-propenoate

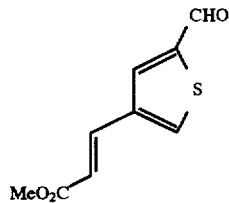

Compound 37 was prepared in 88% yield. ¹HMR (400 MHz, CDCl₃) δ3.79 (s, 3H), 6.30 (d, 1H), 7.60 (d, 1H), 7.81 (s, 1H), 7.88 (s, 1H), 9.90 (s, 1H).

Experimental Procedure for the Synthesis of Imidazoles

The proper dione, aldehyde and ammonium acetate were placed in acetic acid. Mixture was heated to 80°–140° C. for 0.5–4 hours. It was then cooled to room temperature. The pH of solution was adjusted to 0.8 using 3.0M hydrochloric acid. It was then extracted with ether (5 times) to remove the unreacted aldehyde and dione). The aqueous layer was neutralized to pH 8 with 3M sodium hydroxide and extracted with methylenechloride (3 times). The organic layers were dried (N₂SO₄) and evaporated to give the corresponding imidazole compound.

EXAMPLES

Example 38

2-[4-(trans-i-propylpropenoate)phenyl]-4,5-bis[(4-N,N-dimethylamino)phenyl] imidazole:

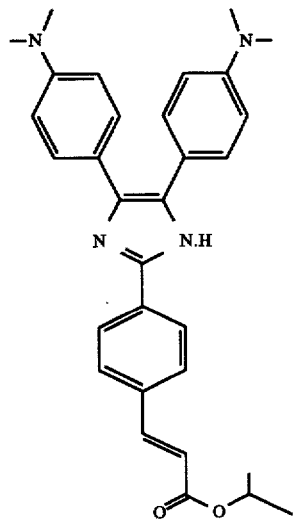

Compound 38 was prepared according to method C in 82% yield by using the proper dione and aldehyde. Compound 38 has: ¹H NMR (400 MHz, CD₃OD) δ1.30 (d, 6H), 3.10 (s, 12H), 5.08 (m, 1H), 6.68 (d, 1H), 7.40 (d, 4H), 7.62 (d, 4H), 7.72 (d, 1H), 7.90 (d, 2H), 8.10 (d, 2H); ESIMS, m/z for C₃₁H₃₄O₂N₄ [M+H]⁺: 495.

Example 39

2-[4-(trans-t-butylpropenoate)phenyl]-4,5-bis[(4-N,N-dimethylamino)phenyl] imidazole:

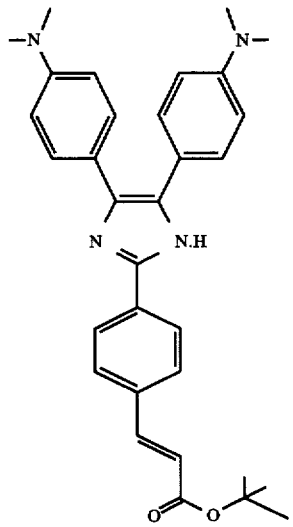
(39)

Compound 39 was prepared according to method C in 75% yield by using the proper dione and aldehyde. Compound 39 has: ¹H NMR (400 MHz, CDCl₃ with a little CD₃OD) δ1.40 (s, 9H), 2.90 (s, 12H), 6.22 (d, 1H), 6.58 (d, 4H), 7.38 (m, 7H), 7.80 (br s, 2H).

Example 40

2-[4-(trans-methylpropenoate)phenyl]-4-[(4-N,N-diethylamino)phenyl]-5-[(4-N-methylamino)phenyl] imidazole:

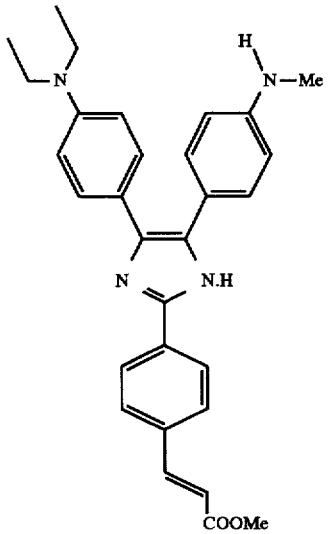
(40)

Compound 40 was prepared according to method C in 87% yield by using the proper dione and aldehyde. Compound 40 has: ¹H NMR (400 MHz, CD₃OD) δ1.10 (t, 6H), 2.78 (s, 3H), 3.38 (m, 4H), 3.78 (s 3H), 6.56–6.66 (m, 5H), 7.25 (m, 4H), 7.58–7.72 (m, 3H), 7.93 (d, 2H); ESIMS, m/z for C₃₀H₃₂O₂N₄ [M+H]⁺: 493.

Example 41

2-[4-(trans-i-propylpropenoate)phenyl]-4-[(4-N,N-diethylamino)phenyl]-5-[(4-N-methylamino)phenyl] imidazole:

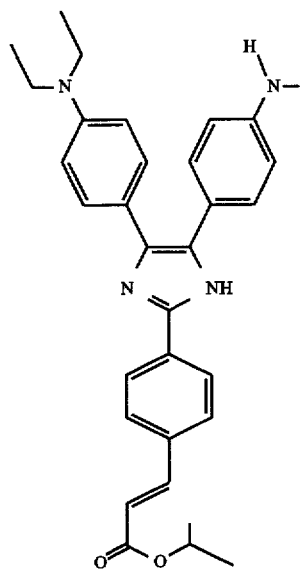
(41)

Compound 41 was prepared according to method C in 85% by using the proper dione and aldehyde. Compound 41 has: ¹H NMR (400 MHz, CD₃OD) δ1.14 (t, 6H), 1.30 (d, 6H), 2.78 (s, 3H), 3.38 (m, 4H), 5.08 (m, 1H), 6.50 (d, 1H), 6.58 (d, 2H), 6.64 (d, 2H), 7.28 (m, 4H), 7.62 (m, 3H), 7.98 (d, 2H); ESIMS, m/z for C₃₂H₃₆O₂N₄ [M+H]⁺: 509.

Example 42

2-[4-(trans-methylpropenoate)phenyl]-4-[(4-N,N-dimethylamino)phenyl]-5-[(4-N-methylamino)phenyl] imidazole:

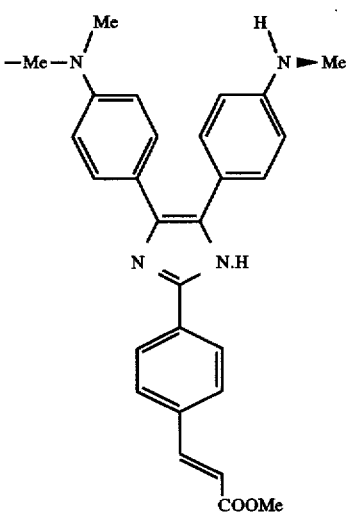
(42)

Compound 42 was prepared according to method C in 93% yield by using the proper dione and aldehyde. Compound 42 has: ¹H NMR (400 MHz, CDCl₃) δ2.77 (s, 3H), 2.89 (s, 6H), 3.74 (s, 3H), 6.35 (d, 1H), 6.50 (d, 2H), 6.62 (d, 2H), 7.35 (m, 4H), 7.41 (d, 2H), 7.59 (d, 1H), 7.81 (d, 2H); ESIMS, m/z for C₂₈H₂₈O₂N₄ [M+H]⁺: 453.

Example 43

2-[4-(trans-methylpropenoate)phenyl]-4-[(4-N-methyl-N-propylamino)phenyl]-5-[(4-N-methylamino)phenyl] imidazole:

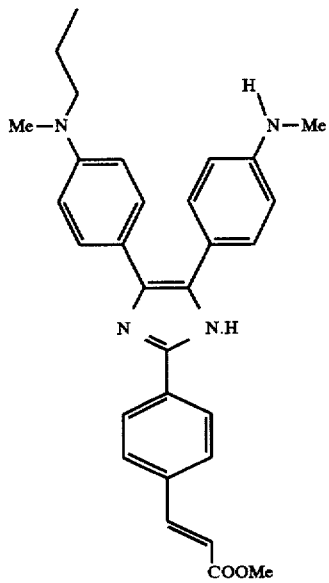

(43)

Compound 43 was prepared according to method C in 89% yield by using the proper dione and aldehyde. Compound 43 has: 1H NMR (400 MHz, CDCl$_3$) δ0.85 (t, 3H), 1.54 (m, 2H), 2.78 (s, 3H), 2.88 (s, 3H), 3.22 (s, 2H), 3.74 (s, 3H), 6.35 (d, 1H), 6.50 (d, 2H), 6.62 (d, 2H), 7.35 (m, 4H), 7.41 (d, 2H), 7.59 (d, 1H), 7.81 (d, 2H); ESIMS, m/z for C$_{30}$H$_{32}$O$_2$N$_4$ [M+H]$^+$: 481.

Example 44

2-[4-(trans-methylpropenoate)phenyl]-4-[(4-N,N-dipropylamino)phenyl]-5-[(4-N-methylamino) phenyl] imidazole:

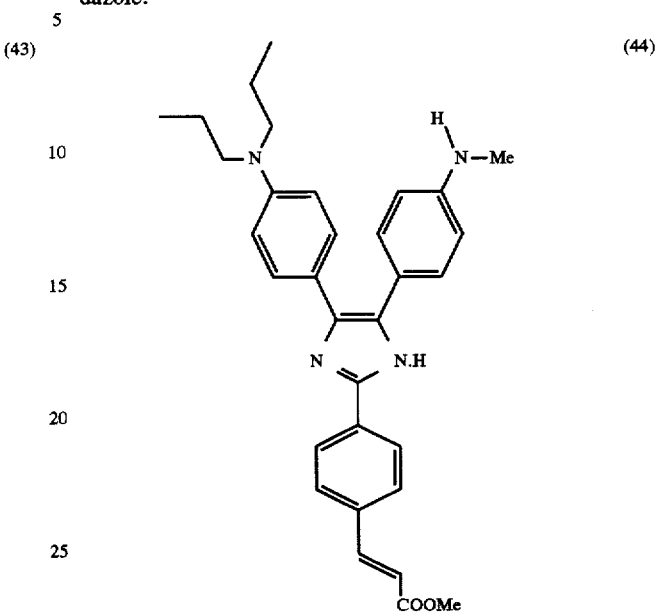

(44)

Compound 44 was prepared according to method C 47% yield by using the proper dione and aldehyde. Compound 44 has: $^1$H NMR (400 MHz, CDCl$_3$) δ0.85 (t, 6H), 1.54 (m, 4H), 2.80 (s, 3H), 3.20 (s, 4H), 3.74 (s, 3H), 6.35 (d, 1H), 6.50 (d, 2H), 6.62 (d, 2H), 7.35 (m, 4H), 7.41 (d, 2H), 7.59 (d, 1H), 7.81 (d, 2H); ESIMS, m/z for C$_{32}$H$_{36}$O$_2$N$_4$ [M+H]$^+$: 509.

Example 45

2-[4-(trans-methylpropenoate)phenyl]-4-[(4-N,N-dibutylamino)phenyl]-5-[(4-N-methylamino)phenyl] imidazole:

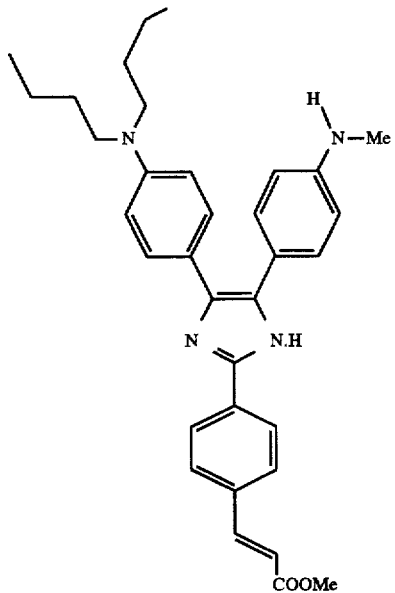

(45)

Compound 45 was prepared according to method C in 68% by using the proper dione and aldehyde. Compound 45 has: $^1$H NMR (400 MHz, CDCl$_3$) δ0.91 (t, 6H), 1.31 (m, 4H), 1.52 (m, 4H), 2.81 (s, 3H), 3.22 (t, 4H), 3.74 (s, 3H), 6.40 (d, 1H), 6.55 (m, 4H), 7.38 (m, 4H), 7.50 (d, 2H), 7.64 (d, 1H), 7.84 (d, 2H); ESIMS, m/z for C$_{34}$H$_{40}$O$_2$N$_4$ [M+H]$^+$: 537.

Example 46

2-[4-(trans-methylpropenoate)phenyl]-4,5-bis(4-N-methylaminophenyl) imidazole:

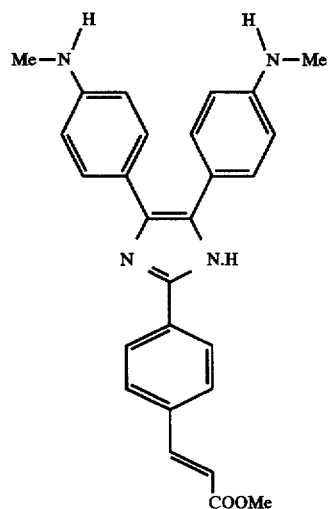

(46)

Compound 46 was prepared according to method C in 70% by using the proper dione and aldehyde. Compound 46 has: $^1$H NMR (400 MHz, CD$_3$OD) δ2.75 (s, 6H), 3.76 (s, 3H), 6.53 (d, 1H), 6.56 (d, 4H), 7.24 (d, 4H), 7.65 (d, 2H), 7.68 (d, 4H) 7.96 (d, 2H); ESIMS, m/z for C$_{27}$H$_{26}$O$_2$N$_4$ [M+H]$^+$: 437.

Example 47

2-[4-(trans-methylpropenoate)phenyl]-4-[(4-N-i-propylamino)phenyl]-5-[(4-N-methylamino)phenyl] imidazole:

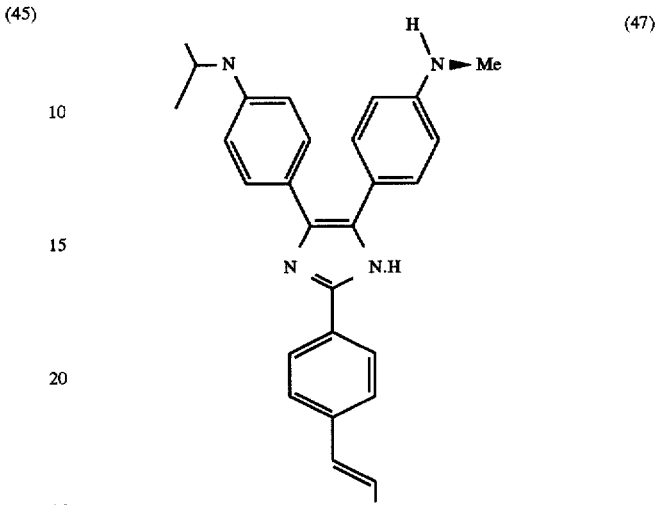

(47)

Compound 47 was prepared according to method C in 65% by using the proper dione and aldehyde. Compound 47 has: $^1$H NMR (400 MHz, CD$_3$OD) δ1.30 (d, 6H), 2.94 (s, 3H), 3.78 (m, 4H), 6.70 (d, 1H), 6.90 (d, 2H), 7.39 (d, 4H), 7.64 (d, 2H), 7.78 (d, 1H), 7.90 (d, 2H), 8.06 (d, 2H); ESIMS, m/z for C$_{29}$H$_{30}$O$_2$N$_4$ [M+H]$^+$: 467.

Example 48

2-[4-(trans-methylpropenoate)phenyl]-4-[(4-N-t-butylamino)phenyl]-5-[(4-N-methylamino)phenyl] imidazole:

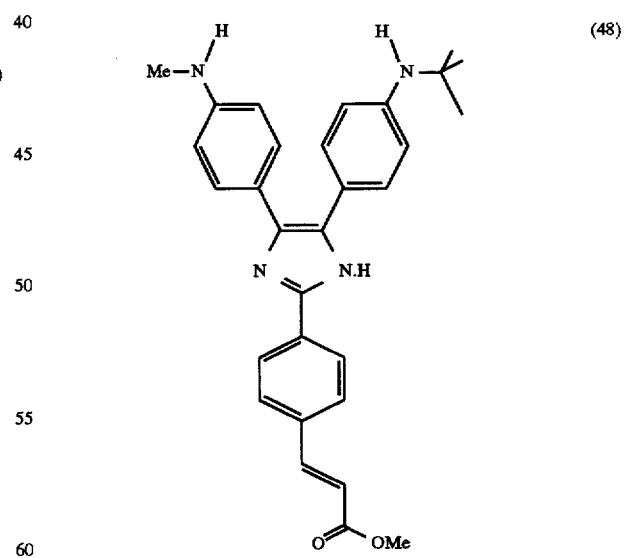

(48)

Compound 48 was prepared according to method C in 51% yield by using the proper dione and aldehyde. Compound 48 has: $^1$H NMR (400 MHz, CDCl$_3$) δ1.30 (s, 9H), 2.80 (s, 3H), 3.78 (s, 3H), 6.38 (d, 1H), 6.52 (d, 2H), 6.65 (d, 2H), 7.33 (m, 4H), 7.47 (d, 2H), 7.62 (d, 1H), 7.83 (d, 2H); ESIMS, m/z for C$_{30}$H$_{32}$O$_2$N$_4$ [M+H]$^+$: 481.

Example 49

2-[4-(trans-methylpropenoate)phenyl]-4,5-bis(4-N,N-diethylaminophenyl) imidazole:

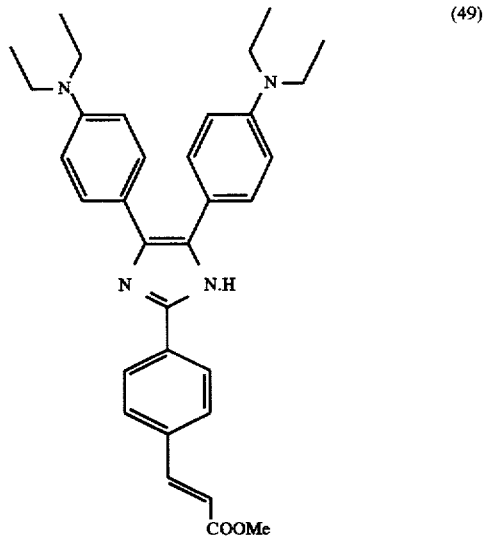
(49)

Compound 49 was prepared according to method C in 91% by using the proper dione and aldehyde. Compound 49 has: $^1$H NMR (400 MHz, CDCl$_3$) δ1.14 (t, 12H), 3.30 (s, 8H), 3.79 (s, 3H), 6.50 (m, 5H), 7.50 m, 9H).

Example 50

2-[4-(trans-methylpropenoate)phenyl]-4-[(4-N,N-diethylamino)phenyl]-5-[(4-N,N-dimethylamino)phenyl] imidazole:

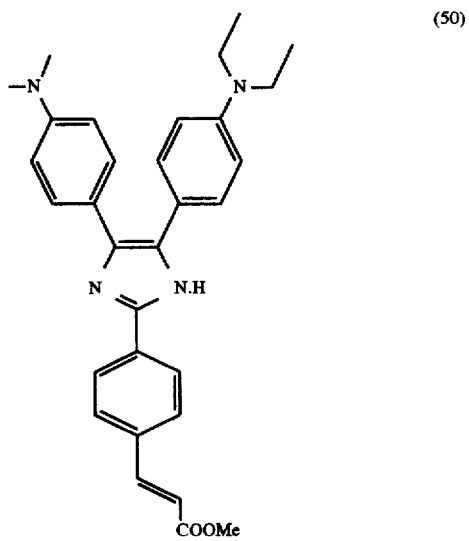
(50)

Compound 50 was prepared according to method C in 34% yield by using the proper dione and aldehyde. Compound 50 has: $^1$H NMR (400 MHz, CDCl$_3$) δ1.14 (t, 6H), 2.93 (s, 6H), 3.33 (s, 4H), 3.79 (s, 3H), 6.50 (m, 5H), 7.50 (m, 9H); ESIMS, m/z for C$_{31}$H$_{34}$O$_2$N$_4$ [M+H]$^+$: 495.

Example 51

2-[4-(trans-methylpropenoate)phenyl]-4-[(4-N,N-dimethylamino)phenyl]-5-(4-aminophenyl) imidazole:

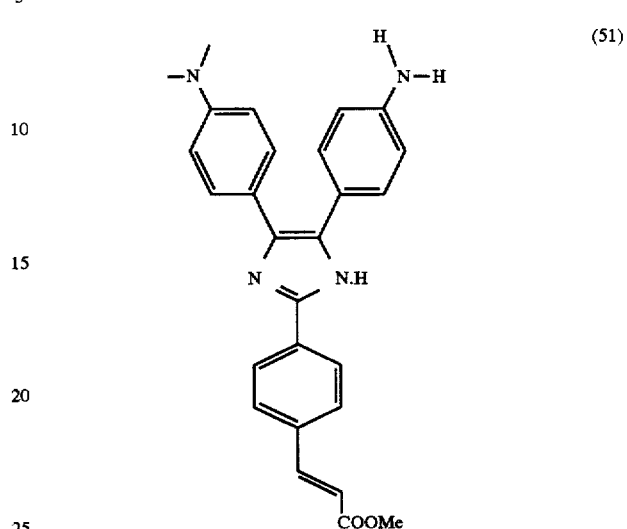
(51)

Compound 51 was prepared according to method C in 43% yield by using the proper dione and aldehyde. Compound 51 has: $^1$H NMR (400 MHz, CDCl$_3$) δ2.95 (s, 6H), 3.78 (s, 3H), 6.42 (d, 1H), 6.64 (m, 4H), 7.38 (br s, 4H), 7.53 (d, 2H), 7.66 (d, 1H), 7.86 (d, 2H); ESIMS, m/z for C$_{27}$H$_{26}$O$_2$N$_4$ [M+H]$^+$: 439.

Example 52

2-[4-(trans-methylpropenoate)phenyl]-4-[(4-N,N-diethylamino)phenyl]-5-(4-aminophenyl) imidazole:

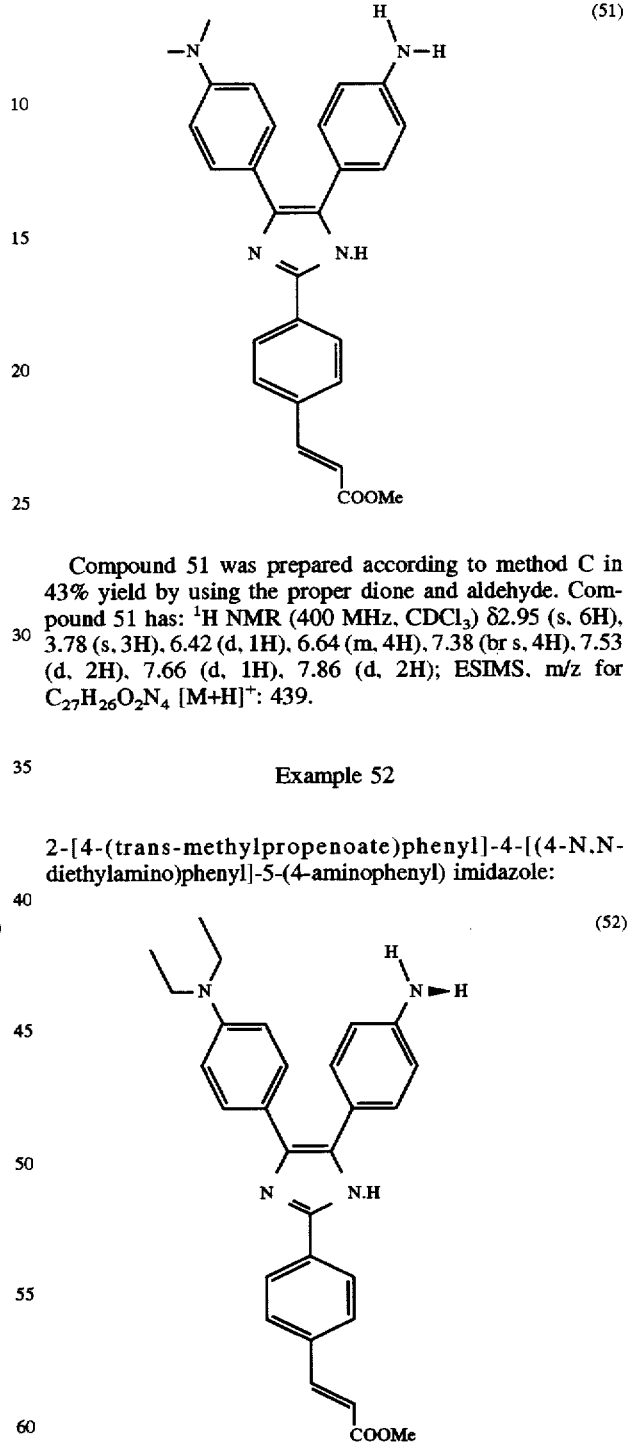
(52)

Compound 52 was prepared according to method C in 30% yield by using the proper dione and aldehyde. Compound 52 has: $^1$H NMR (400 MHz, CDCl$_3$) δ1.13 (t, 6H), 3.32 (m, 4H), 3.78 (s, 3H), 6.40 (d, 1H), 6.64 (m, 4H), 7.38 (br s, 4H), 7.53 (d, 2H), 7.66 (d, 1H), 7.86 (d, 2H).

Example 53

2-[4-(trans-methylpropenoate)phenyl]-4-[(4-N-methylamino)phenyl]-5-(4-fluorophenyl) imidazole:

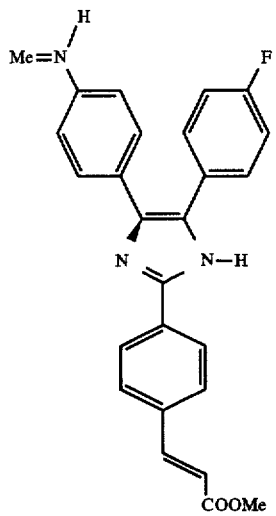

(53)

Compound 53 was prepared according to method C in 58% yield by using the proper dione and aldehyde. Compound 53 has: $^1$H NMR (400 MHz, CD$_3$OD) δ2.78 (s, 3H), 3.78 (s, 3H), 6.54 (d, 1H), 6.58 (d, 2H), 7.01 (m, 2H), 7.18 (d, 2H), 7.48 (d, 2H), 7.67 (m, 3H), 7.96 (d, 2H); ESIMS, m/z for C$_{26}$H$_{22}$O$_2$N$_3$F [M+H]$^+$: 428.

Example 54

2-[3-(trans-methylpropenoate)phenyl]-4,5-bis(4-N,N-dimethylaminophenyl) imidazole:

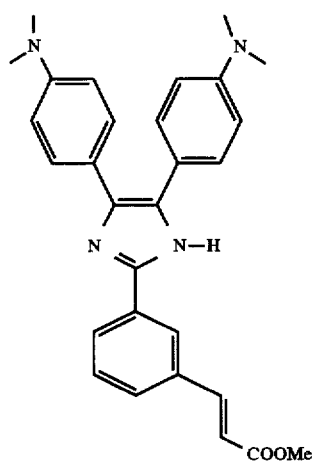

(54)

Compound 54 was prepared according to method C quantitatively by using the proper dione and aldehyde. Compound 54 has: $^1$H NMR (400 MHz, CD$_3$OD) δ2.91 (s, 12H), 3.76 (s, 3H), 6.63 (d, 1H), 6.71 (d, 4H), 7.31 (d, 4H), 7.46 (dd, 1H), 7.56 (d, 1H), 7.72 (d, 1H), 7.95 (d, 1H), 8.21 (s, 1H); ESIMS, m/z for C$_{29}$H$_{30}$O$_2$N$_4$ [M+H]$^+$: 467.

Example 55

2-[4-methoxy-3-(trans-methylpropenoate)phenyl]-4,5-bis(4-N,N-dimethylaminophenyl) imidazole:

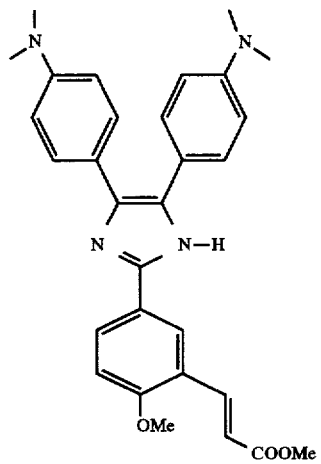

(55)

Compound 55 was prepared according to method C quantitatively by using the proper dione and aldehyde. Compound 55 has: $^1$H NMR (400 MHz, CD$_3$OD) δ2.90 (s, 12H), 3.75 (s, 3H), 3.92 (s, 3H), 6.46 (d, 1H), 6.71 (d, 4H), 7.10 (d, 1H), 7.30 (d, 4H), 7.96 (dd, 1H), 8.00 (d, 1H), 8.22 (s, 1H); ESIMS, m/z for C$_{30}$H$_{32}$O$_3$N$_4$ [M+H]$^+$: 497.

Example 56

2-[2-methoxy-5-(trans-methylpropenoate)phenyl]-4,5-bis(4-N,N-dimethylaminophenyl) imidazole:

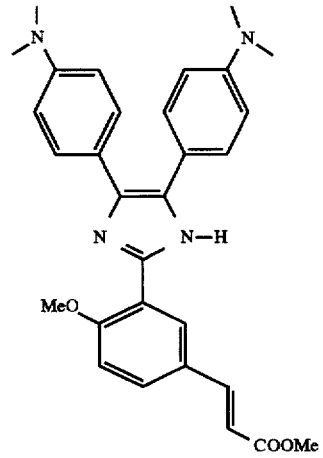

(56)

Compound 56 was prepared according to method C 56% by using the proper dione and aldehyde. Compound 56 has: $^1$H NMR (400 MHz, CD$_3$OD) δ2.90 (s, 12H), 3.75 (s, 3H), 4.00 (s, 3H), 6.48 (d, 1H), 6.70 (d, 4H), 7.12 (d, 1H), 7.31 (d, 4H), 7.53 (d, 1H), 7.66 (d, 1H), 8.31 (s, 1H); ESIMS, m/z for C$_{30}$H$_{32}$O$_3$N$_4$ [M+H]$^+$: 497.

Example 57

2-[3,4-dimethoxy-5-(trans-methylpropenoate)phenyl]-4,5-bis(4-N,N-dimethylaminophenyl) imidazole:

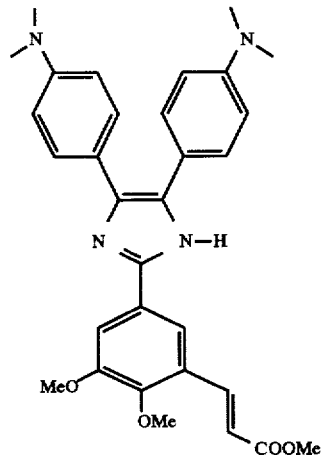
(57)

Compound 57 was prepared according to Method C quantitatively by using the proper dione and aldehyde. Compound 57 has: $^1$H NMR (400 MHz, CD$_3$OD) δ2.89 (s, 12H), 3.75 (s, 3H), 3.83 (s, 3H), 3.91 (s, 3H), 6.62 (d, 1H), 6.69 (d, 4H), 7.29 (d, 4H), 7.68 (s, 1H), 7.85 (s, 1H), 7.95 (d, 1H); ESIMS, m/z for C$_{31}$H$_{34}$O$_4$N$_4$ [M+H]$^+$: 527.

Example 58

2-[4-fluoro-3-(trans-methylpropenoate)phenyl]-4,5-bis(4-N,N-dimethylaminophenyl) imidazole:

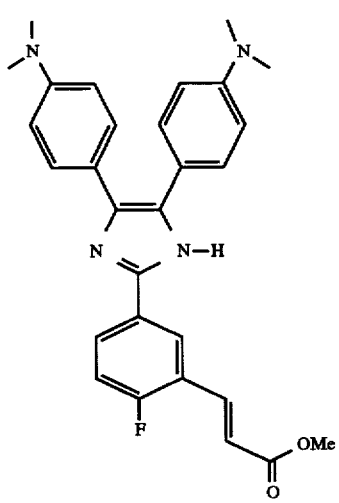
(58)

Compound 58 was prepared according to method A in 20% yield by using the proper dione and aldehyde. Compound 58 has: $^1$H NMR (400 MHz, CD$_3$OD) δ2.90 (s, 12H), 3.78 (s, 3H), 6.74 (d, 4H), 7.20 (d, 6H), 7.82 (d, 1H), 8.00 (m, 1H), 8.32 (d, 1H); ESIMS, m/z for C$_{29}$H$_{29}$O$_2$N$_4$F [M+H]$^+$: 485.

Example 59

2-[4-fluoro-3-(trans-methylpropenoate)phenyl]-4-[(4-N,N-dimethylamino) phenyl]-5-[(4-N-methylamino) phenyl] imidazole:

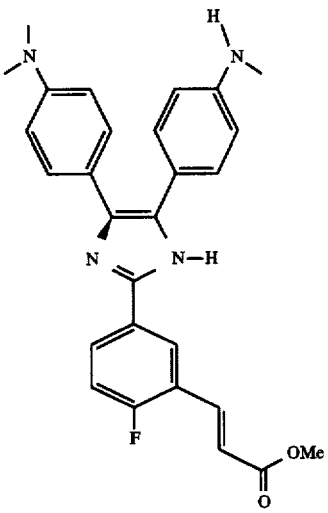
(59)

Compound 59 was prepared according to method C in 15% yield by using the proper dione and aldehyde. Compound 59 has: $^1$H NMR (400 MHz, CD$_3$OD) δ2.78 (s, 3H), 2.92 (s, 6H), 3.78 (s, 3H), 6.56 (d, 2H), 6.70 (d, 2H), 7.04–7.36 (m, 6H), 7.82 (d, 1H), 7.97 (m, 1H), 8.29 (d, 1H); ESIMS, m/z for C$_{28}$H$_{27}$O$_2$N$_4$F [M+H]$^+$: 471.

Example 60

2-[2-fluoro-4-(trans-methylpropenoate)phenyl]-4,5-bis(4-N,N-dimethylaminophenyl) imidazole:

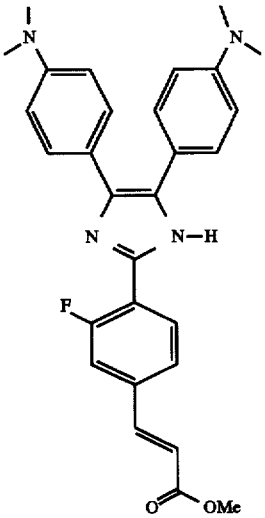
(60)

Compound 60 was prepared according to method C in 17% yield by using the proper dione and aldehyde. Compound 60 has: $^1$H NMR (400 MHz, CD$_3$OD) δ2.91 (s, 9H), 3.06 (s, 3H), 3.76 (s, 3H), 6.59 (d, 1H), 6.71 (d, 4H), 7.31 (d, 4H), 7.50 (d, 1H), 7.66 (d, 1H), 7.71 (d, 1H), 7.97 (dd, 1H); ESIMS, m/z for C$_{29}$H$_{29}$O$_2$N$_4$F [M+H]$^+$: 485.

Example 61
2-[4-(trans-methylpropenoate)thienyl]-4,5-bis[(4-N,N-dimethylamino)phenyl] imidazole:

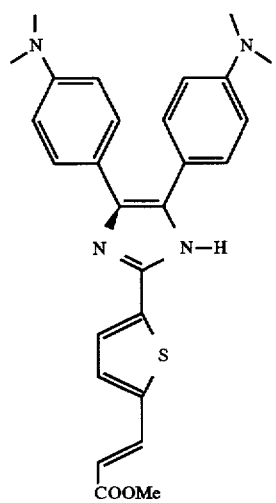

(61)

Compound 61 was prepared according to method C quantitatively by using the proper dione and aldehyde. Compound 61 has: $^1$H NMR (400 MHz, CD$_3$OD) δ2.91 (s, 12H), 3.74 (s, 3H), 6.25 (d, 1H), 6.70 (d, 4H), 7.30 (m, 5H), 7.48 (d, 1H), 7.76 (d, 1H); ESIMS, m/z for C$_{27}$H$_{28}$O$_2$N$_4$S [M+H]$^+$: 473.

Example 62
2-[3-(trans-methylpropenoate)thienyl]-4,5-bis[(4-N,N-dimethylamino)phenyl] imidazole:

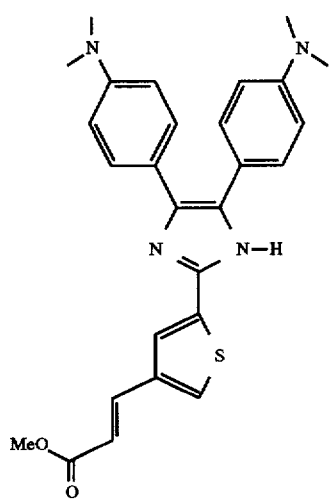

(62)

Compound 62 was prepared according to method C in 63% yield by using the proper dione and aldehyde. Compound 62 has: $^1$H NMR (400 MHz, CD$_3$OD) δ2.90 (s, 12H), 3.75 (s, 3H), 6.34 (d, 1H), 6.69 (d, 4H), 7.28 (d, 4H), 7.62 (d, 1H), 7.67 (d, 1H), 7.78 (s, 1H); ESIMS, m/z for C$_{27}$H$_{28}$O$_2$N$_4$S [M+H]$^+$: 473.

Example 63
2-[4-(3-methoxypropyl)phenyl]-4,5-bis[(4-N,N-dimethylamino)phenyl] imidazole:

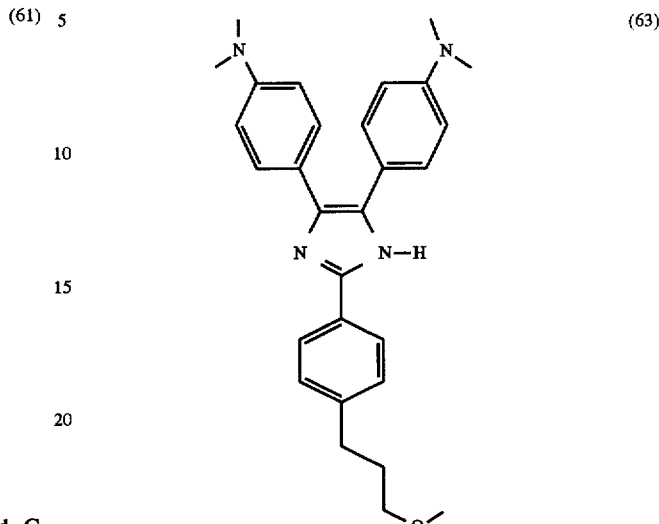

(63)

Compound 63 was prepared according to method C quantitatively by using the proper dione and aldehyde. Compound 63 has: $^1$H NMR (400 MHz, CD$_3$OD) δ1.82 (m, 2H), 2.64 (m, 2H), 2.89 (s, 12H), 3.28 (s, 3H), 3.38 (t, 2H), 6.64 (d, 4H), 7.28 (m, 6H), 7.80 (d, 2H); ESIMS, m/z for C$_{29}$H$_{34}$ON$_4$ [M+H]$^+$: 455.

Example 64
2-[2-methoxy-5-(trans-i-propylpropenoate)phenyl]-4,5-bis(4-N,N-dimethylaminophenyl) imidazole:

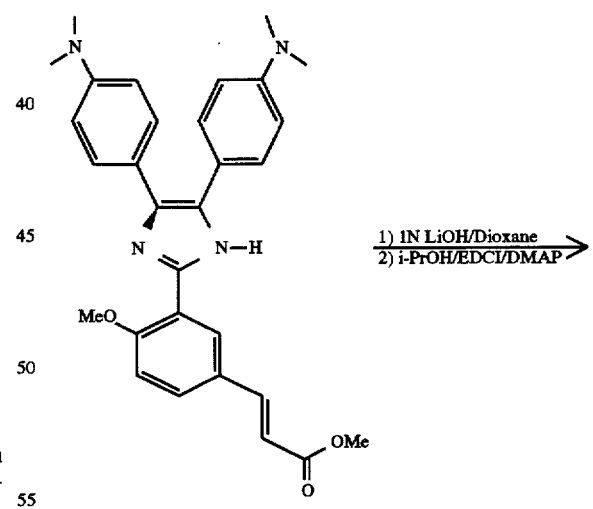

1) 1N LiOH/Dioxane
2) i-PrOH/EDCI/DMAP (56)

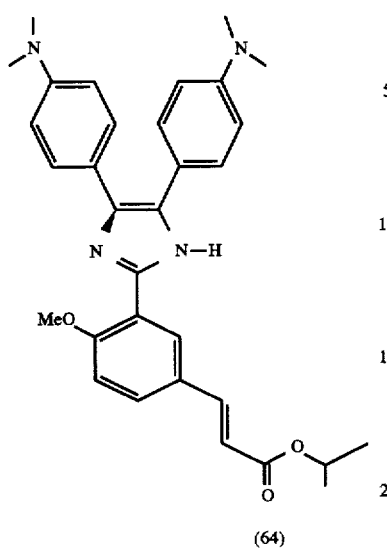

(64)

A suspension of compound 56 (408 mg, 0.82 mmol) in a mixture of 1N aqueous LiOH (5.0 mL) and 1,4-dioxane (10.0 mL) was heated (100° C.) for 3 h, during which time it turned to a clear solution. It was then cooled to room temperature (23° C.) and neutralized with 1N HCl to pH 4.5. The mixture was extracted with ethyl acetate and the organic layer was dried ($Na_2SO_4$) and evaporated to obtain the crude carboxylic acid. To a solution of the crude material thus obtained in a solvent mixture of isopropanol and dichloromethane (1:1, 10 mL), were added EDCI (235 mg, 1.23 mmol), and DMAP (75 mg, 0.61 mmol). The resulting solution was stirred at room temperature (23° C.) overnight. It was then diluted with dichloromethane and washed with water. The organic layer was dried ($Na_2SO_4$), and evaporated. Flash chromatography of the residue over silica gel gave the desired product as a yellow solid (61%). Compound 64 has: $^1$H NMR (400 MHz, $CD_3OD$) δ1.26 (d, 6H), 2.90 (s, 12H), 4.98 (s, 3H), 5.05 (m, 1H), 6.45 (d, 1H), 6.71 (d, 4H), 7.12 (d, 1H), 7.30 (d, 4H), 7.54 (d, 1H), 7.63 (d, 1H), 8.27 (s, 1H); ESIMS, m/z for $C_{32}H_{36}O_3N_4$ [M+H]$^+$: 525.

Example 65
2-[3-(trans-i-propylpropenoate)thienyl]-4,5-bis[(4-N,N-dimethylamino)phenyl] imidazole:

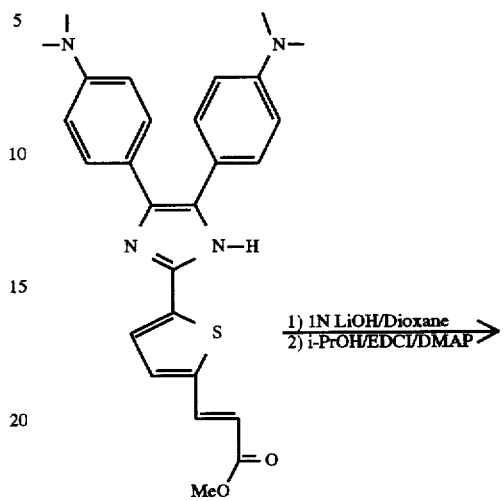

(61)

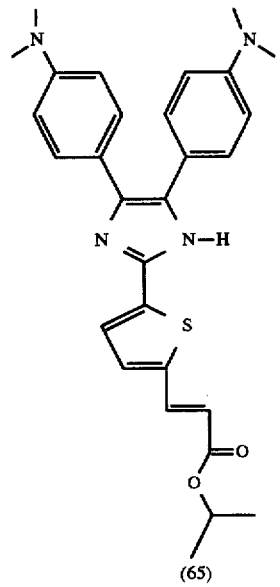

(65)

This compound was prepared in the same way as compound 64 in 70% yield. Compound 65 has: $^1$H NMR (400 MHz, $CD_3OD$) δ1.24 (d, 6H), 2.91 (s, 12H), 3.74 (s, 3H), 5.04 (m, 1H), 6.25 (d, 1H), 6.70 (d, 4H), 7.30 (m, 5H), 7.48 (d, 1H), 7.76 (d, 1H); ESIMS, m/z for $C_{29}H_{32}O_2N_4S$ [M+H]$^+$: 501.

Example 67

2-[4-(trans-benzylpropenoate)phenyl]-4,5-bis[(4-N,N-dimethylamino)phenyl] imidazole:

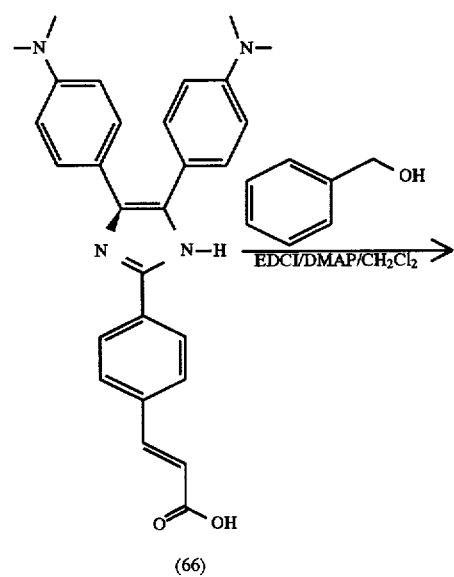

(66)

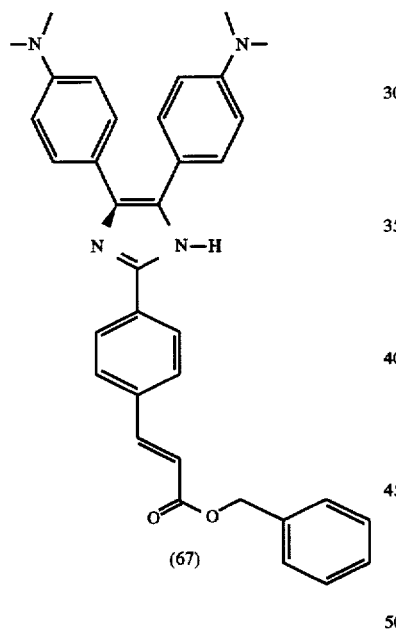

(67)

Compound 66 was prepared according to method C by using the proper dione and aldehyde. Compound 67 was then prepared from compound 66 via conventional ester coupling procedure (75% yield). Compound 67 has: $^1$H NMR (400 MHz, CD$_3$OD) δ2.90 (s, 12H), 5.10 (s, 2H), 6.54 (d, 1H), 6.70 (d, 4H), 7.34 (m, 9H), 7.62 (d, 2H), 7.70 (d, 1H), 7.98 (d, 2H).

Example 68

2-[4-(trans-phenethylpropenoate)phenyl]-4,5-bis[(4-N,N-dimethylamino)phenyl] imidazole:

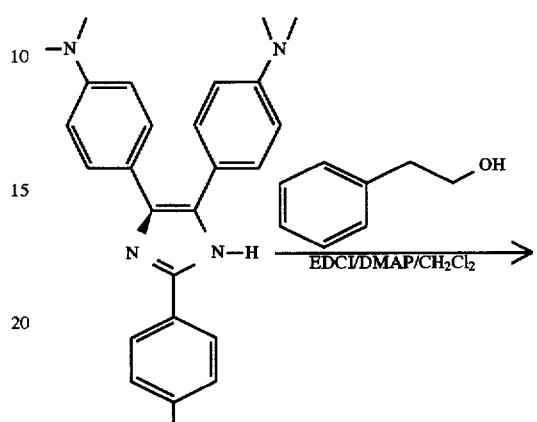

(66)

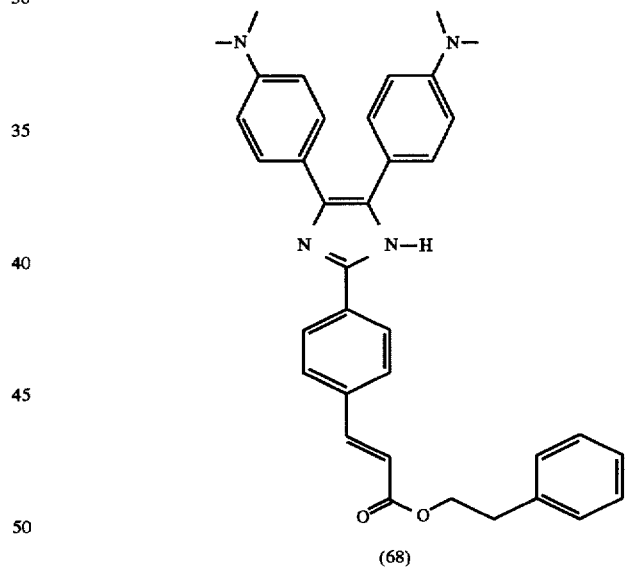

(68)

Compound 68 was prepared according to method in example 67 in 72% yield. Compound 68 has: $^1$H NMR (400

MHz, CD₃OD) δ2.90 (m, 14H), 4.38 (t, 2H), 6.54 (d, 1H), 6.70 (d, 4H), 7.30 (m, 9H), 7.62 (d, 1H), 7.70 (d, 2H), 7.98 (d, 2H).

Example 69

2-[4-(3-ethoxypropyl)phenyl]-4,5-bis[(4-N,N-dimethylamino)phenyl] imidazole:

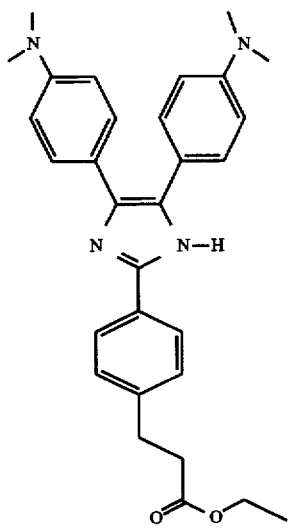

(69)

Compound 69 was prepared according to method C quantitatively by using the proper dione and aldehyde. Compound 69 has: ¹H NMR (400 MHz, CD₃OD) δ1.16 (t, 3H), 1.86 (m, 2H), 2.69 (t, 2H), 2.90 (s, 12H), 3.45 (m, 4H), 6.71 (d, 4H), 7.25 (d, 2H), 7.30 (d, 4H), 7.83 (d, 2H); ESIMS, m/z for C₃₀H₃₆ON₄ [M+H]⁺: 469.

Example 70

2-[4-butyloxyphenyl]-4,5-bis[(4-N,N-dimethylamino)phenyl] imidazole:

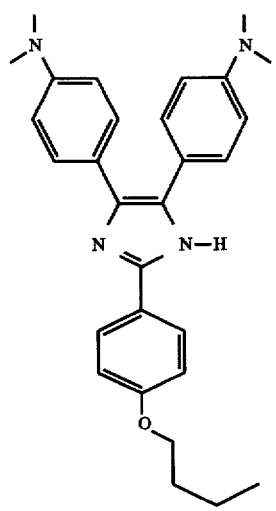

70

Compound 70 was prepared according to method C in 60% yield by using the proper dione and aldehyde. Compound 70 has: ¹H NMR (400 MHz, CD₃OD) δ0.94 (t, 3H), 1.45 (m, 2H), 1.71 (m, 2H), 2.85 (s, 12H), 3.92 (t, 2H), 6.65 (d, 4H), 6.90 (d, 2H), 7.27 (d, 4H), 7.79 (d, 2H); ESIMS, m/z for C₂₉H₃₄ON₄ [M+H]⁺: 455.

Example 71

2-[4-(2-methoxyethoxy)phenyl]-4,5-bis[(4-N,N-dimethylamino)phenyl] imidazole:

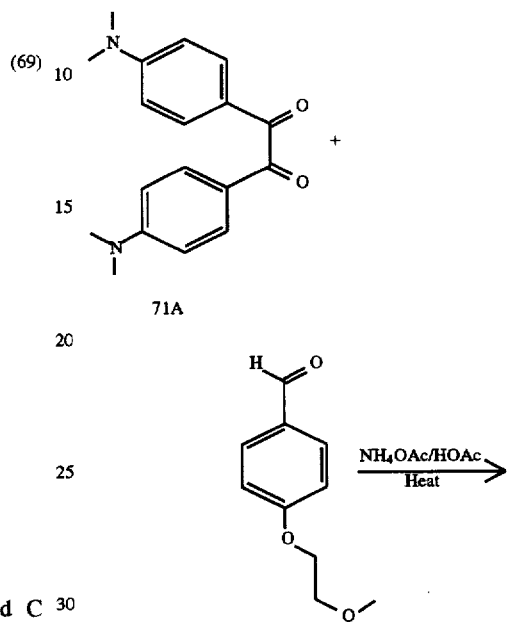

71A

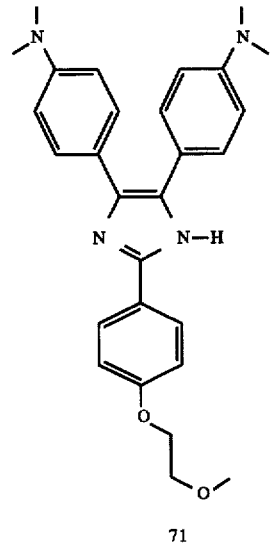

71

Aldehyde 71A was simply prepared by alkylating 4-hydroxybenzaldehyde with 2-bromoethyl methyl ether/NaH in DMF.

Compound 71 was prepared according to method C in 71% yield by using the proper dione and aldehyde. Compound 71 has: ¹H NMR (400 MHz, CD₃OD) δ2.84 (s, 12H), 3.36(s, 3H), 3.68 (t, 2H), 4.06 (t, 2H), 6.64 (d, 4H), 6.93 (d, 2H), 7.27 (d, 4H), 7.80 (d, 2H); ESIMS, m/z for C₂₈H₃₂O₂N₄ [M+H]⁺: 457.

Example 72
2-[3-methoxy-4-(2-methoxyethoxy)-phenyl]-4,5-bis[(4-N,N-dimethylamino)phenyl] imidazole:

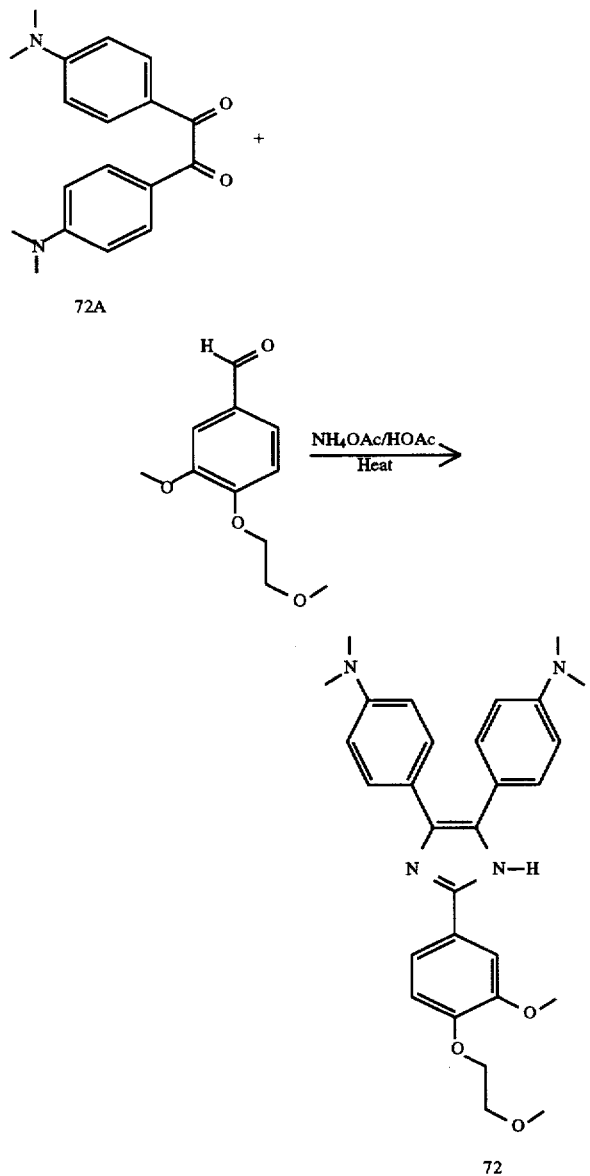

Aldehyde 72A was simply prepared by alkylating 4-hydroxy-3-methoxy-benzaldehyde with 2-bromoethyl methyl ether/NaH in DMF.

Compound 72 was prepared according to method C in 71% yield by using the proper dione and aldehyde. Compound 72 has: $^1$H NMR (400 MHz, CD$_3$OD) δ2.86 (s, 12H), 3.36(s, 3H), 3.68 (t, 2H), 3.84 (s, 3H), 4.08 (t, 2H), 6.65 (d, 4H), 6.93 (d, 1H), 7.27 (d, 4H), 7.43 (d, 1H), 7.57 (s, 1H); ESIMS, m/z for C$_{29}$H$_{34}$O$_3$N$_4$ [M+H]$^+$: 487.

The compounds described herein are capable of sensitizing multi-drug resistant tumor cells to antitumor chemotherapeutic agents, such as doxorubicin and vinblastine. They also have the ability to potentiate the sensitivity of tumor cells susceptible to these chemotherapeutic agents. This invention also relates to a method of sensitizing multidrug-resistant tumor cells to antitumor chemotherapeutic agents. It also relates to a method of increasing the sensitivity of drug-susceptible tumor cells to antitumor chemotherapeutic agents. In addition, this invention relates to a method of preventing the emergence of MDR tumor cells during a course of treatment with antitumor chemotherapeutic agents. Finally, this invention relates to a method of reducing the effective dosage of an antitumor chemotherapeutic agent during a course of treatment. It has been found that compounds of Formula 1 have the ability to increase the sensitivity of MDR mammalian cells in culture.

Cytotoxic drugs are commonly used as antitumor chemotherapeutic agents. These agents are also called antiproliferative agents. The desired effect of cytotoxic drugs is selective cell death with destruction of the malignant neoplastic cells and relative sparing of normal cells.

Cytotoxic drugs have also proved valuable in the treatment of other neoplastic disorders including connective or autoimmune diseases, metabolic disorders, dermatological diseases, and DNA virus infections.

Proper use of cytotoxic drugs requires a thorough familiarity with the natural history and pathophysiology of the disease before selecting the cytotoxic agent, determining a dose, and undertaking therapy. Each patient must be carefully evaluated, with attention directed toward factors which may potentiate toxicity, such as overt or occult infections, bleeding dyscrasias, poor nutritional status, and severe metabolic disturbances. In addition, the functional condition of certain major organs, such as liver, kidneys, and bone marrow, is extremely important. Therefore, the selection of the appropriate cytotoxic agent and devising an effective therapeutic regimen is influenced by the presentation of the patient.

Cytotoxic drugs as antitumor chemotherapeutic agents can be subdivided into several broad categories, including, (1) alkylating agents, such as mechlorethamine, cyclophosphamide, melphalan, uracil mustard, chlorambucil, busulfan, carmustine, lomustine, semustine, streptozoticin, and decrabazine; (2) antimetabolites, such as methotrexate, fluorouracil, fluorodeoxyuridine, cytarabine, azarabine, idoxuridine, mercaptopurine, azathioprine, thioguanine, and adenine arabinoside; (3) natural product derivatives, such as vinblastine, vincristine, dactinomycin, daunorubicin, doxorubicin, mithramycin, bleomycin, etoposide, teniposide, and mitomycin-C; and (4) miscellaneous agents, such as hydroxyurea, procarbezine, mititane, and cis-platinum.

Important antitumor chemotherapeutic agents (with the usual effective dosage) to which clinical multidrug-resistance has been observed include vinblastine (0.1 mg per kilogram per week), vincristine (0.01 mg per kilogram per week), etoposide (35 to 50 mg per square meter per day), dactinomycin (0.15 mg per kilogram per day), doxorubicin (500 to 600 mg per square meter per week), daunorubicin (65 to 75 mg per square meter per week), and mithramycin (0.025 mg per kilogram per day). MDR has been shown to occur in vitro as well as in the clinic.

Multidrug-resistant cell lines are easily obtainable for in vitro determination of drug sensitization by compounds of the present invention. In vitro potentiation of antineoplastic cytotoxicity by the imidazole derivatives of the present invention was measured in both CEM/VLB1000 and SK/VLB1000 cell lines. The multidrug resistant cell lines were obtained from Dr. Victor Ling, Ontario Cancer Institute, Toronto, Canada. The CEM/VLB 1000 cell line was maintained as a suspension in minimum essential medium supplemented with 10% fetal bovine serum in a humidied atmosphere of 95% air and 5% CO$_2$ while the SK/VLB 1000 cell line was maintained as adherent cells using the identical medium conditions as the CEM cells. The CEM/VLB 1000 cells were seeded at a density of 5×10$^4$ cells/well in a 96 well microtiter plate while the SK/VLB 1000 cell line was seeded at a density of 2,500 cells/well after trypsinization. Vinblastine (5 µg/mL, for the CEM cells) or Taxol (3 µg/mL, for the SK cells) and compound (0.01 to 50 µM) were added directly to the wells. After an incubation of 48 hours in presence of drug, alamar blue (B. Page et al., *Int. J. Oncol.* 3: 473–476, 1993) was added (10 µL to the 200 µL cell suspension) for a period of 24 hours after which the fluorescence (excitation=530 nM, emission= 590 nM) was read for each well using a "CytoFluor" microtiter fluorometer plate reader. This assay measures the effective concentration of compound necessary to enhance the cytotoxicity ($EC_{50}$) of vinblastine in the MDR cell line. The compounds of the present invention had $EC_{50}$ values in the range of 0.06 to 10 µM.

$^3$H-vinblastine accumulation was also measured in the CEM/VLB1000 cell line. Corning Easy-Wash 96 well plates were pretreated with PBS and 1% BSA for 60 minutes and then removed. CEM/VLB1000 cells were seeded at $2 \times 10^5$, 40 µL volume. Plates were incubated at 37° C. for 30–60 minutes prior to use. The reference reversing agent, verapamil, or the compound of the present invention was added to the well followed by addition of media containing $^3$H-vinblastine (final concentration=275 nM). Plates were allowed to incubate for 3 hours at 37° C. Cells were harvested onto pretreated Wallace filtermats A (pretreated with 0.1% polyethyleneimine) using a TomTek harvester-96. After filtering, the filtermats were allowed to dry completely. Meltix B scintillant was then added to the filtermats. The filters were then placed in a 90° C. oven for approximately 3–5 minutes and then removed. Scintillant was allowed to solidify on the filtermats. Filtermats were then placed in sample bags and read on a Wallace BetaPlate scintillation counter. The effects of compounds of the present invention in the cytotoxicity potentiation assays and vinblastine (VLB) accumulation assay are given in the Table below:

| Examples | Cytotoxicity Potentiation (µM)[2] CEM/VLB1000 | [$^3$H]VLB Accumulation (µM)[2] CEM/VLB1000 |
|---|---|---|
| 38 | 0.138 | 2.4 |
| 39 | 0.59 | 4.5 |
| 40 | 0.226 | 1.1 |
| 41 | 0.42 | 6.0 |
| 42 | 0.17 | 1.1 |
| 43 | 0.148 | 2.3 |
| 44 | 0.165 | 1.4 |
| 45 | 1.9 | 10.0 |
| 46 | 0.203 | 1.4 |
| 47 | 0.194 | 0.87 |
| 48 | 0.24 | 1.2 |
| 49 | 0.675 | 5.0 |
| 50 | 0.225 | 4.9 |
| 51 | 0.48 | 2.6 |
| 52 | 0.275 | 2.6 |
| 53 | 0.63 | 6.5 |
| 54 | 0.256 | 4.8 |
| 55 | 0.37 | 6.0 |
| 56 | 0.126 | 2.8 |
| 57 | 0.453 | 2.8 |
| 58 | 0.134 | 2.0 |
| 59 | 0.57 | 3.2 |
| 60 | 0.613 | 3.0 |
| 61 | 0.217 | 1.8 |
| 62 | 0.320 | 3.0 |
| 63 | 0.205 | 1.1 |
| 64 | 0.390 | 6.0 |
| 65 | 0.211 | 4.0 |
| 67 | 0.33 | 10.5 |
| 68 | 1.20 | >30 |
| 69 | 0.21 | NT[3] |
| 70 | 0.43 | NT |
| 71 | 0.17 | NT |
| 72 | 0.16 | NT |

[1]Values presented are the midpoint ($EC_{50}$) of the minimum and maximum cytotoxicity induced by 3–5 µg/mL vinblastine and the specific compound of the present invention.
[2]Values presented are the midpoint ($EC_{50}$) of the minimum and maximum increase in accumulation of $^3$H-vinblastine caused by the specific compound of the present invention.
[3]NT = Not tested.

The modulation of multidrug-resistance demonstrated by the imidazole derivatives described herein provides a method of treatment of multidrug-resistant tumors. The multidrug-resistance modulatory properties of the compounds described herein also provides a method for the prevention of the emergence of multi-drug resistant tumors during the course of cancer treatment. These same compounds additionally provide a method for reducing the required dosage of an antitumor chemotherapeutic agent.

All of the methods of this invention involve (1) the administration of a compound of Formula 1 prior to, together with, or subsequent to the administration of an antitumor chemotherapeutic agent; and (2) the administration of a combination of a compound of Formula 1 and an antitumor chemotherapeutic agent.

Thus, the compounds of Formula 1 are useful in the treatment of multidrug-resistant tumor cells or tumor cells in general, either separately or in combination with an antitumor chemotherapeutic agent. These compounds may be administered orally, topically or parenterally in dosage unit formulations containing conventional non-toxic pharmaceutically acceptable carriers, adjuvants, and vehicles. The term parenteral as used herein includes subcutaneous injections, intravenous, intramuscular, intrasternal injection or infusion techniques.

The present invention also has the objective of providing suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. The tablets contain the acting ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such expicients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In adition, fatty acids such as oleic acid find use in the preparation of injectables.

A compound of Formula 1 may also be administered in the form of suppositories for rectal administration of the drug. These compositions can be prepared by mixing the drug with a suitable non-irritating excipient which is solid at ordinary temperature but liquid at the rectal temperature and will therefore melt in the rectum to release the drug. Such materials are cocoa butter and polyethylene glycols.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds of Formula 1 are employed.

Dosage levels of the compounds of the present invention are of the order of about 0.5 mg to about 100 mg per kilogram body weight, with a preferred dosage range between about 20 mg to about 50 mg per kilogram body weight per day (from about 25 mg to about 5 gms per patient per day). The amount of active ingredient that may be combined with the carrier materials to produce a single dosage will vary depending upon the host treated and the particular mode of administration. For example, a formulation intended for oral administration to humans may contain 5 mg to 1 g of an active compound with an appropriate and convenient amount of carrier material which may vary from about 5 to about 95 percent of the total composition. Dosage unit forms will generally contain between from about 5 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula 1, and as such are not intended to limit the invention as set forth in the claims appended thereto. Furthermore, the compounds described in the following examples are not to be construed as forming the only genus that is considered as the invention, and any combination of the compounds or their moieties may itself form a genus. The structure and purity of all final products were assured by at least one of the following methods: thin-layer chromatography (TLC), mass spectroscopy, nuclear magnetic resonance (NMR) spectroscopy, or combustion analysis. NMR data is in the form of delta (d) values for major diagnostic protons, given in parts per million (ppm) relative to tetramethylsilane (TMS) as internal standard, determined at 400 MHz in deuteriochloroform ($CDCl_3$); conventional abbreviations used for signal shape are: s, singlet; d, doublet; t, triplet; m, multiplet; br., broad; etc. The following abbreviations have also been used: v (volume), w (weight), L (liter), mL (milliliter), g (gram), mg (milligram), mol (moles), mmol (millimoles), equiv (equivalents).

What is claimed is:

1. A compound of the formula 1

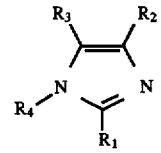

Formula 1 wherein:

$R_1$ is selected from the group consisting of: mono-,di-,and tri-substituted phenyl or thienyl, the substituents are selected from the group consisting of:
(i) substituted $C_{1-6}$ alkyl, substituted $C_{2-6}$ alkyloxy, wherein the substituents are selected from the group consisting of hydrogen or $C_{1-6}$ alkoxy;
(ii) $C_{1-11}CO_2R_5$, trans-CH=$CHCO_2R_5$, wherein $R_5$ is $C_{1-11}$ alkyl, or phenyl $C_{1-11}$ alkyl;

$R_2$ and $R_3$ are mono-, di, and tri-substituted phenyl wherein the substituents are independently selected from:
(i) halo;
(ii) $C_{1-6}$ alkyl-amino, or di($C_{1-6}$ alkyl)amino, with the proviso that $R_2$ and $R_3$ cannot be simultaneously a halo-substituted phenyl and $R_4$ is hydrogen;

or the pharmaceutically acceptable salts thereof.

2. A compound according to claim 1 wherein $R_1$ is 4-[(trans-2-isopropyloxycarbonyl)-ethenyl]-phenyl; $R_2$ and $R_3$ are 4-(dimethylamino)-phenyl; and $R_4$ is hydrogen.

3. A compound according to claim 1 wherein $R_1$ is 4-[(trans-2-tert-butyloxycarbonyl)-ethenyl]-phenyl; $R_2$ and $R_3$ are 4-(dimethylamino)-phenyl; and $R_4$ is hydrogen.

4. A compound according to claim 1 wherein $R_1$ is 4-[(trans-2-methoxycarbonyl)-ethenyl]-phenyl; $R_2$ is 4-(methylamino)-phenyl and $R_3$ are 4-(diethylamino)-phenyl; and $R_4$ is hydrogen.

5. A compound according to claim 1 wherein $R_1$ is 4-[(trans-2-isopropyloxycarbonyl)-ethenyl]-phenyl; $R_2$ is 4-(methylamino)-phenyl and $R_3$ are 4-(diethylamino)-phenyl; and $R_4$ is hydrogen.

6. A compound according to claim 1 wherein $R_1$ is 4-[(trans-2-methoxycarbonyl)-ethenyl]-phenyl; $R_2$ is 4-(methylamino)-phenyl and $R_3$ are 4-(dimethylamino)-phenyl; and $R_4$ is hydrogen.

7. A compound according to claim 1 wherein $R_1$ is 4-[(trans-2-methoxycarbonyl)-ethenyl]-phenyl; $R_2$ is 4-(methylamino)-phenyl and $R_3$ are 4-(n-propylmethylamino)-phenyl; and $R_4$ is hydrogen.

8. A compound according to claim 1 wherein $R_1$ is 4-[(trans-2-methoxycarbonyl)-ethenyl]-phenyl; $R_2$ is 4-(methylamino)-phenyl and $R_3$ are 4-di(n-propylamino)-phenyl; and $R_4$ is hydrogen.

9. A compound according to claim 1 wherein $R_1$ is 4-[(trans-2-methoxycarbonyl)-ethenyl]-phenyl; $R_2$ is 4-(methylamino)-phenyl and $R_3$ are 4-di(n-butylamino)-phenyl; and $R_4$ is hydrogen.

10. A compound according to claim 1 wherein $R_1$ is 4-[(trans-2-methoxycarbonyl)-ethenyl]-phenyl; $R_2$ and $R_3$ are 4-(methylamino)-phenyl; and $R_4$ is hydrogen.

11. A compound according to claim 1 wherein $R_1$ is 4-[(trans-2-methoxycarbonyl)-ethenyl]-phenyl; $R_2$ is 4-(isopropylamino)-phenyl and $R_3$ are 4-(methylamino)-phenyl; and $R_4$ is hydrogen.

12. A compound according to claim 1 wherein $R_1$ is 4-[(trans-2-methoxycarbonyl)-ethenyl]-phenyl; $R_2$ is 4-(tert-butylamino)-phenyl and $R_3$ are 4-(methylamino)-phenyl; and $R_4$ is hydrogen.

13. A compound according to claim 1 wherein $R_1$ is 4-[(trans-2-methoxycarbonyl)-ethenyl]-phenyl; $R_2$ and $R_3$ are 4-di(ethylamino)-phenyl; and $R_4$ is hydrogen.

14. A compound according to claim 1 wherein $R_1$ is 4-[(trans-2-methoxycarbonyl)-ethenyl]-phenyl; $R_2$ is 4-di(ethylamino)-phenyl and $R_3$ are 4-di(methylamino)-phenyl; and $R_4$ is hydrogen.

15. A compound according to claim 1 wherein $R_1$ is 4-[(trans-2-methoxycarbonyl)-ethenyl]-phenyl; $R_2$ is 4-(amino)-phenyl and $R_3$ are 4-di(methylamino)-phenyl; and $R_4$ is hydrogen.

16. A compound according to claim 1 wherein $R_1$ is 4-[(trans-2-methoxycarbonyl)-ethenyl]-phenyl; $R_2$ is 4-(amino)-phenyl and $R_3$ are 4-di(ethylamino)-phenyl; and $R_4$ is hydrogen.

17. A compound according to claim 1 wherein $R_1$ is 4-[(trans-2-methoxycarbonyl)-ethenyl]-phenyl; $R_2$ is 4-(fluoro)-phenyl and $R_3$ are 4-(methylamino)-phenyl; and $R_4$ is hydrogen.

18. A compound according to claim 1 wherein $R_1$ is 3-[(trans-2-methoxycarbonyl)-ethenyl]-phenyl; $R_2$ and $R_3$ are 4-di(methylamino)-phenyl; and $R_4$ is hydrogen.

19. A compound according to claim 1 wherein $R_1$ is 3-[(trans-2-methoxycarbonyl)-ethenyl]-4-methoxy-phenyl; $R_2$ and $R_3$ are 4-di(methylamino)-phenyl; and $R_4$ is hydrogen.

20. A compound according to claim 1 wherein $R_1$ is 5-[(trans-2-methoxycarbonyl)-ethenyl]-2-methoxy-phenyl; $R_2$ and $R_3$ are 4-di(methylamino)-phenyl; and $R_4$ is hydrogen.

21. A compound according to claim 1 wherein $R_1$ is 5-[(trans-2-methoxycarbonyl)-ethenyl]-3,4-dimethoxy-phenyl; $R_2$ and $R_3$ are 4-di(methylamino)-phenyl; and $R_4$ is hydrogen.

22. A compound according to claim 1 wherein $R_1$ is 3-[(trans-2-methoxycarbonyl)-ethenyl]-4-fluoro-phenyl; $R_2$ and $R_3$ are 4-di(methylamino)-phenyl; and $R_4$ is hydrogen.

23. A compound according to claim 1 wherein $R_1$ is 3-[(trans-2-methoxycarbonyl)-ethenyl]-4-fluoro-phenyl; $R_2$ is 4-(methylamino)-phenyl; and $R_3$ is 4-di(methylamino)-phenyl; and $R_4$ is hydrogen.

24. A compound according to claim 1 wherein $R_1$ is 4-[(trans-2-methoxycarbonyl)-ethenyl]-2-fluoro-phenyl; $R_2$ and $R_3$ are 4-di(methylamino)-phenyl; and $R_4$ is hydrogen.

25. A compound according to claim 1 wherein $R_1$ is 4-[(trans-2-methoxycarbonyl)-ethenyl]-thienyl; $R_2$ and $R_3$ are 4-di(methylamino)-phenyl; and $R_4$ is hydrogen.

26. A compound according to claim 1 wherein $R_1$ is 3-[(trans-2-methoxycarbonyl)-ethenyl]-thienyl; $R_2$ and $R_3$ are 4-di(methylamino)-phenyl; and $R_4$ is hydrogen.

27. A compound according to claim 1 wherein $R_1$ is 4-(n-propyl-methylether)-phenyl; $R_2$ and $R_3$ are 4-di(methylamino)-phenyl; and $R_4$ is hydrogen.

28. A compound according to claim 1 wherein $R_1$ is 5-[(trans-2-isopropyloxycarbonyl)-ethenyl]-2-methoxy-phenyl; $R_2$ and $R_3$ are 4-di(methylamino)-phenyl; and $R_4$ is hydrogen.

29. A compound according to claim 1 wherein $R_1$ is 4-[(trans-2-isopropyloxycarbonyl)-ethenyl]-thienyl; $R_2$ and $R_3$ are 4-di(methylamino)-phenyl; and $R_4$ is hydrogen.

30. A compound according to claim 1 wherein $R_1$ is 4-[(trans-2-benzyloxycarbonyl)-ethenyl]-phenyl; $R_2$ and $R_3$ are 4-di(methylamino)-phenyl; and $R_4$ is hydrogen.

31. A compound according to claim 1 wherein $R_1$ is 4-[(trans-2-phenylethyloxycarbonyl)-ethenyl]-phenyl; $R_2$ and $R_3$ are 4-di(methylamino)-phenyl; and $R_4$ is hydrogen.

32. A compound according to claim 1 wherein $R_1$ is 4-(3-ethoxypropyl)-phenyl; $R_2$ and $R_3$ are 4-di(methylamino)-phenyl; and $R_4$ is hydrogen.

33. A compound according to claim 1 wherein $R_1$ is 4-butyloxyphenyl; $R_2$ and $R_3$ are 4-di(methylamino)phenyl; and $R_4$ is hydrogen.

34. A compound according to claim 1 wherein $R_1$ is 4-(2-methoxyethoxy)phenyl; $R_2$ and $R_3$ are 4-di(methylamino)-phenyl; and $R_4$ is hydrogen.

35. A compound according to claim 1 wherein $R_1$ is 3-methoxy-4-(2-methoxyethoxy)-phenyl; $R_2$ and $R_3$ are 4-di(methylamino)-phenyl; and $R_4$ is hydrogen.

36. A method of treatment for increasing the sensitivity of tumor cells to anti-cancer chemotherapeutic agents, said tumor cells being susceptible to anticancer chemotherapeutic agents, and said tumor cells having become resistant to chemotherapy comprising administration to a mammalian species in need of such treatment a therapeutically effective amount of a compound of claim 1 and a pharmaceutically acceptable carrier.

37. A method of treatment of tumor cells, said tumor cells being susceptible to anti-cancer chemotherapeutic agents, and said tumor cells having become resistant to chemotherapy comprising: administration to a mammalian species in need of such treatment, of a therapeutically effective amount of said anti-cancer chemotheratic agent, and an effective amount of a compound of claim 1.

38. A method of treatment of tumor cells according to claim 37 comprising: administration to a mammalian species in need of such treatment a therapeutically effective amount of an anti-cancer chemotherapeutic agent selected from the group consisting of taxol, vinblastine, vincristine, daunorubicin, and doxorubicin.

39. A pharmaceutical composition for increasing the sensitivity of tumor cells to anti-cancer chemotherapeutic agents, said tumors cells having become resistant to chemotherapy comprising a therapeutically effective amount of a compound of claim 1 and a pharmaceutically acceptable carrier.

40. A pharmaceutical composition for increasing the sensitivity of tumor cells to anti-cancer chemotherapeutic agents, said tumors cells having become resistant to chemotherapy comprising: a therapeutically effective amount of an anti-cancer chemotherapeutic agent selected from the group consisting of taxol, vinblastine, vincristine, daunorubicin, and doxorubicin, an effective amount of a compound of claim 1, and a pharmaceutically acceptable carrier.

* * * * *